United States Patent
Heshmat Dehkordi et al.

(10) Patent No.: US 10,386,650 B2
(45) Date of Patent: Aug. 20, 2019

(54) METHODS AND APPARATUS FOR HIGH RESOLUTION IMAGING WITH REFLECTORS AT STAGGERED DEPTHS BENEATH SAMPLE

(71) Applicant: Massachusetts Institute of Technology, Cambridge, MA (US)

(72) Inventors: Barmak Heshmat Dehkordi, San Mateo, CA (US); Albert Redo-Sanchez, Zizur Mayor (ES); Gordon Moseley Andrews, Boston, MA (US); Ramesh Raskar, Palo Alto, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 45 days.

(21) Appl. No.: 15/791,025

(22) Filed: Oct. 23, 2017

(65) Prior Publication Data

US 2018/0113321 A1 Apr. 26, 2018

Related U.S. Application Data

(60) Provisional application No. 62/411,586, filed on Oct. 22, 2016.

(51) Int. Cl.
*G01B 9/02* (2006.01)
*G01N 21/47* (2006.01)
(Continued)

(52) U.S. Cl.
CPC ......... *G02B 27/58* (2013.01); *G01B 9/02018* (2013.01); *G01B 9/02024* (2013.01);
(Continued)

(58) Field of Classification Search
CPC ........... G01N 21/3586; G01N 21/4795; G01N 2021/4797; G01N 21/031;
(Continued)

(56) References Cited

U.S. PATENT DOCUMENTS

| 5,710,430 A | 1/1998 | Nuss |
| 7,136,155 B2* | 11/2006 | Kong ................... G01N 21/643 356/70 |

(Continued)

OTHER PUBLICATIONS

Brunner, Fabian D.J. et al. "A terahertz time-domain spectrometer for simultaneous transmission and reflection measurements at normal incidence". Optics Express, vol. 17, No. 23, Nov. 9, 2009, pp. 20684-20693. (Year: 2009).*

(Continued)

*Primary Examiner* — Michael A Lyons
(74) *Attorney, Agent, or Firm* — Stephen R. Otis

(57) ABSTRACT

A sample may be illuminated in such a way that light passes through the sample, reflects from a set of reflectors, passes through the sample again and travels to a light sensor. The reflectors may be staggered in depth beneath the sample, each reflector being at a different depth. Light reflecting from each reflector, respectively, may arrive at the light sensor during a different time interval than that in which light reflecting from other reflectors arrives—or may have a different phase than that of light reflecting from the other reflectors. The light sensor may separately measure light reflecting from each reflector, respectively. The reflectors may be extremely small, and the separate reflections from the different reflectors may be combined in a super-resolved image. The super-resolved image may have a spatial resolution that is better than that indicated by the diffraction limit.

2 Claims, 24 Drawing Sheets
(11 of 24 Drawing Sheet(s) Filed in Color)

(51) Int. Cl.
  G02B 27/10    (2006.01)
  G02B 27/58    (2006.01)
  G01N 21/3586  (2014.01)
(52) U.S. Cl.
  CPC ..... *G01B 9/02025* (2013.01); *G01B 9/02091* (2013.01); *G01N 21/3586* (2013.01); *G01N 21/4795* (2013.01); *G02B 27/1066* (2013.01); *G01N 2021/4797* (2013.01)
(58) Field of Classification Search
  CPC ... G01N 2021/0314; G01N 2021/5992; G02B 27/1066; G02B 27/58; G01B 9/02018; G01B 9/02024
  See application file for complete search history.

(56)  References Cited

U.S. PATENT DOCUMENTS

| | | | |
|---|---|---|---|
| 7,826,504 | B2 | 11/2010 | Chen et al. |
| 2006/0049356 | A1 | 3/2006 | Shen et al. |
| 2007/0235658 | A1* | 10/2007 | Zimdars ............ G01J 3/42 250/390.07 |
| 2008/0165355 | A1 | 7/2008 | Yasui et al. |
| 2009/0303574 | A1* | 12/2009 | Gunter ............ G01N 21/3581 359/328 |
| 2009/0310138 | A1* | 12/2009 | Vanhanen ......... G01N 21/8507 356/433 |

OTHER PUBLICATIONS

Krishnamurthy, S. et al. "Characterization of thin polymer films using terahertz time-domain interferometry". Applied Physics Letters, vol. 79, No. 6, Aug. 6, 2001, pp. 875-877. (Year: 2001).*

Ung, Benjamin S.-Y. et al. "Dual-Mode Terahertz Time-Domain Spectroscopy System". IEEE Transactions on Terahertz Science and Technology, vol. 3, No. 2, Mar. 2013, pp. 216-220. (Year: 2013).*

Bhandari, A. et al., Super-Resolution in Phase Space; published in arXiv 1501.07662 (Jan. 30, 2015).

Chen, H. et al., Terahertz imaging with nanometer resolution; published in Applied Physics Letters, vol. 83, Issue 15 (Oct. 2003).

Goda, K. et al., Serial time-encoded amplified imaging for real-time observation of fast dynamic phenomena; published in Nature 458, 1145-1149 (Apr. 30, 2009).

Heshmat, B. et al., Nanoplasmonic Terahertz Photoconductive Switch on GaAs; published in Nano Letters, 2012, 12 (12), pp. 6255-6259 (Nov. 21, 2012).

Karpowicz, N. et al., Comparison between pulsed terahertz time-domain imaging and continuous wave terahertz imaging; published in Semiconductor Science and Technology, vol. 20, No. 7 (Jun. 2005).

Lanzano, L., et al., Encoding and decoding spatio-temporal information for super-resolution microscopy; published in Nature Communications 6, Article No. 6701 (Apr. 2015).

Redo-Sanchez, A. et al., Terahertz time-gated spectral imaging for content extraction through layered structures; published in Nat Communications, 2016; 7: 12665 (Sep. 9, 2016).

Yu, C. et al., The potential of terahertz imaging for cancer diagnosis: A review of investigations to date; published in Quantative Imaging in Medicine and Surgery, Mar. 2012; 2(1): 33-45 (Mar. 2012).

Zhao, J. et al., Terahertz imaging with sub-wavelength resolution by femtosecond laser filament in air; published in Scientific Reports 4, Article No. 3880 (Jan. 2014).

Zhao, Z. et al., Going far beyond the near-field diffraction limit via plasmonic cavity lens with high spatial frequency spectrum off-axis illumination; published in Scientific Reports 5:15320 (Oct. 19, 2015).

* cited by examiner

METHODS AND APPARATUS FOR HIGH RESOLUTION IMAGING WITH REFLECTORS AT STAGGERED DEPTHS BENEATH SAMPLE

RELATED APPLICATIONS

This application claims the benefit of U.S. Provisional Application No. 62/411,586, filed Oct. 22, 2016 (the "Provisional Application"), the entire disclosure of which is herein incorporated by reference.

FIELD OF TECHNOLOGY

The present invention relates generally to imaging systems.

COMPUTER PROGRAM LISTING

The following five computer program files are incorporated by reference herein: (1) extend.txt with a size of about 380 bytes; (2) getFFT.txt with a size of about 619 bytes; (3) getThzSuperRes_InterweaveMC.txt with a size of about 575 bytes; (4) InterweaveR.txt with a size of about 266 bytes; and (5) Thz_Subwavelength.txt with a size of about 11,212 bytes. Each of these five files was created as an ASCII .txt file on Oct. 8, 2017.

BACKGROUND

Diffraction creates a limit on imaging resolution. This limit is sometimes called the diffraction barrier. The diffraction barrier for a given imaging system is determined by the optics of the imaging system.

Spatial Resolution: For a conventional imaging system with a numerical aperture NA, two point sources of equal intensity light can be spatially resolved by the system only if the distance between the centers of two spots of light (formed in the image plane by light from the two point sources) is equal to at least the Abbe X-Y Resolution. As used herein, "Abbe X-Y Resolution" means $\lambda/2NA$, where NA is numerical aperture of the imaging system, and $\lambda$ is wavelength. Thus, for any given imaging system with a given numerical aperture, Abbe X-Y Resolution is a limit, imposed by the physical laws of diffraction, on the system's spatial resolution that can be achieved by conventional optics.

SUMMARY

In illustrative implementations of this invention, an imaging system may have a spatial resolution that is better than its Abbe X-Y Resolution. That is, in illustrative implementations of this invention, the system may spatially resolve two locations in a sample being imaged, even though the two locations are so close together that: (a) light reflecting directly back from the two locations in the sample forms two disks of light in the image plane of the system; and (b) the centers of the disks are closer together than the system's Abbe X-Y Resolution.

In illustrative implementations, this dramatically improved spatial resolution is achieved by using light that reflects from a set of reflectors located at staggered depths beneath the sample (instead of light that reflects directly from the sample) and by taking advantage of the ultrafast time resolution of the system. Together, the reflectors and ultrafast time resolution allow the imaging system to "work around" the diffraction barrier.

In illustrative implementations, the reflectors are staggered in depth beneath the sample, in such a way that light reflecting back from the reflectors arrives at a light sensor during a different time interval for each reflector. The light sensor may have ultrafast temporal resolution. Thus, the light sensor may temporally resolve—that is, measure separately during different time intervals—the reflections that arrive at different times from different reflectors. The light sensor may thus acquire a set of separate measurements, each of which, respectively, measures light that reflected from a particular reflector during a particular time interval. The system may then computationally combine these separate measurements to create a spatially super-resolved image.

In illustrative implementations, extremely small reflectors are located beneath the sample being imaged. Each reflector is at a different depth. Horizontally, the reflectors may be arranged in a closed-packed configuration, such as a 2×2 array, 3×3 array or closed-pack set of three reflectors.

In illustrative implementations, light that reflects back from the reflectors (through the sample) arrives at the light sensor at different times for different reflectors (the greater the depth of the reflector, the longer it takes for light to return from the reflector).

In some implementations, a pair of points in the sample may be located so close to each other that the diffraction barrier would prevent a conventional camera from spatially resolving them. However, in illustrative implementations of this invention, if the points are directly above two reflectors (so that each of the points is directly above a different reflector), then the system may (despite the diffraction barrier) spatially resolve these two points. This is because the light sensor may have a sufficiently fast temporal resolution that it may separately measure the reflection from each reflector, respectively (thereby taking advantage of the fact that reflections from different reflectors arrive during different time intervals). The system may computationally combine the separate measurements that were taken during different time intervals into a single, spatially super-resolved image.

In this super-resolved image, there may be a spatially resolved, separately measured light intensity for the tiny x-y region of the sample that is directly above each reflector, respectively—even though the tiny x-y regions that correspond to the reflectors may be so small that the diffraction barrier would ordinarily prevent them from being spatially resolved. Again, this is because a separate measurement may be taken for each reflector (and its corresponding tiny x-y area of the sample), respectively. This ability to measure light from each reflector (and its corresponding tiny x-y region of the sample) separately may arise because: (a) for each reflector, light that reflects from the reflector passes through a corresponding tiny x-y region of the sample (while traveling to and from the reflector); (b) the reflectors are staggered in depth in such a way that light from each reflector (and its corresponding x-y region of the sample), reaches the light sensor of the system during a different time interval; and (c) the light sensor takes a separate measurement during each of these different time intervals. Thus, there may be a separate measurement of light that reflects from each reflector (and its corresponding x-y area of the sample), respectively. Then the separate measurements taken at the separate times may be computationally combined to generate a spatially super-resolved image.

In some cases, the separate measurements for each reflector may be acquired by separating data in post-processing. For example, in some cases, the light sensor may take measurements of reflections over a longer period of time, and then, in post-processing, the system may separate the measurements into shorter time windows, in such a way that each time window corresponds to a time interval in which light from a particular reflector is expected to arrive at the light sensor. For example, in some cases: (a) the light sensor may, for a given position on the sample that is directly above a particular reflector, take a 1D vector of measurements over a longer time period (in which light from all of the reflectors reaches the light sensor); and (b) the system may multiply the 1D vector by a mathematical window function that corresponds to a time window in which light from that particular reflector is expected to arrive at the light sensor.

In illustrative implementations, the system may operate without switchable fluorophores and without near field scanning probes.

This invention is well-suited for high-resolution imaging at lower frequencies (e.g., terahertz or infrared) where the wavelength is longer. For example, many materials have uniquely identifiable features when imaged with terahertz light (such as certain explosives, narcotics, and polymorphic forms of compounds used in drugs). Conventional terahertz imaging tends have low spatial resolution because of (among other things) the longer wavelength of light in the terahertz range. Thus, this invention's ability to acquire super-resolved images in the terahertz range is highly desirable.

For example, in some implementations, the imaging system may employ terahertz time-domain spectroscopy ("THz-TDS") to capture time-resolved images of a temporal sequence of terahertz pulses from the reflectors.

Alternatively, in some implementations, the imaging system may employ optical coherence tomography ("OCT") to capture time-resolved images of a sequence of pulses reflecting from the reflectors. Or, the imaging system may employ OCT to acquire separate measurements of CW (continuous wave) or other non-pulsed light reflecting from each reflector, respectively. The OCT system may separate the CW (or non-pulsed) light that reflects from different reflectors based on the phase of the light (because the phase of the light depends on the round-trip distance that the light travels, which in turn depends on the depth of the reflectors, and thus the phase will be different for each of the reflectors, respectively). In some cases, the OCT imaging system may operate with light in the infrared range or in the visual spectrum.

This invention has many practical applications, including, among other things, super-resolved microscopy imaging, remote sensing, biomedical imaging, industrial noninvasive inspections, water profilometery, and hyperspectral imaging (e.g., in the 5 GHz-500 GHz range of frequencies)

The Summary and Abstract sections and the title of this document: (a) do not limit this invention; (b) are intended only to give a general introduction to some illustrative implementations of this invention; (c) do not describe all of the details of this invention; and (d) merely describe non-limiting examples of this invention. This invention may be implemented in many other ways. Likewise, the description of this invention in the Field of Technology section is not limiting; instead it identifies, in a general, non-exclusive manner, a field of technology to which some implementations of this invention generally relate.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In FIGS. 6C, 6D, 6E, 6F, the light reflected from a first, second, third and fourth reflector, respectively.

Figure 1A:
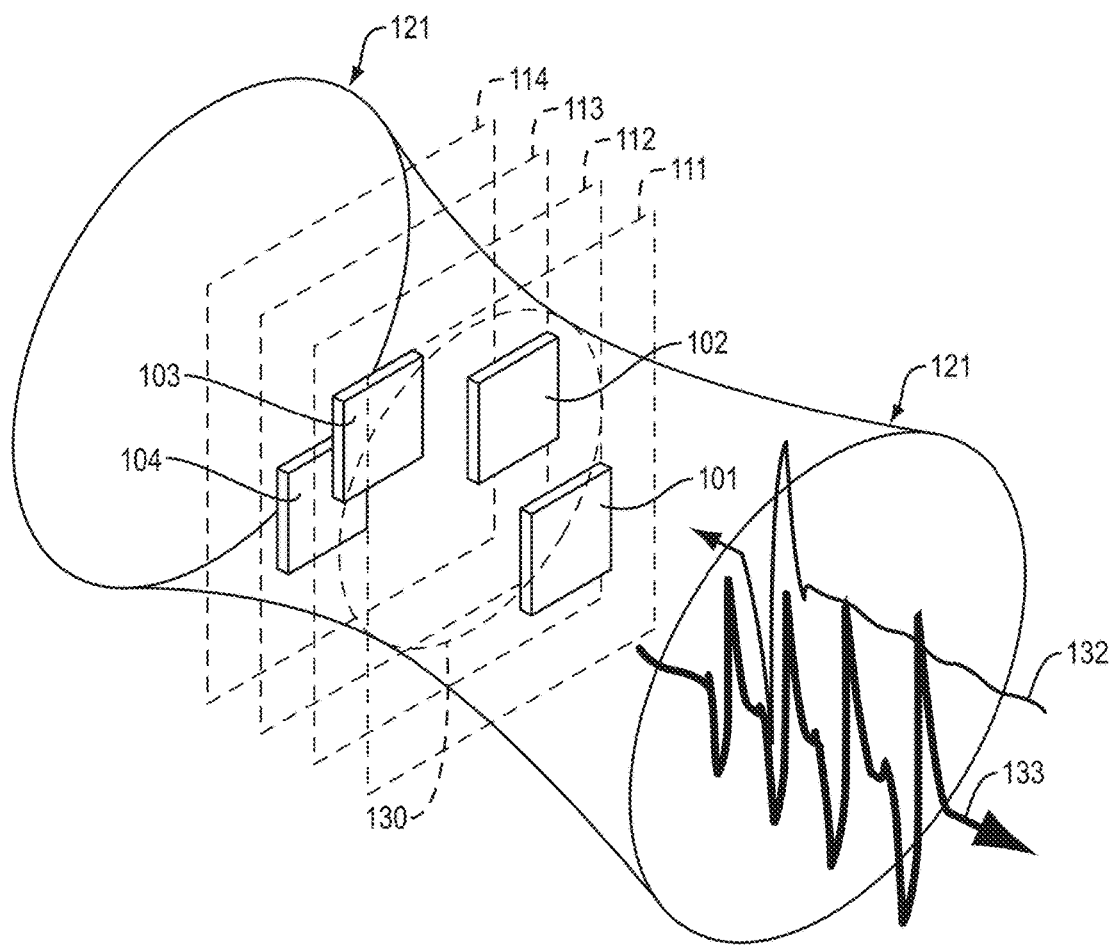
FIG. 1A shows a perspective view of a 2×2 array of reflectors.

The above Figures show some illustrative implementations of this invention, or provide information that relates to those implementations. The examples shown in the above Figures do not limit this invention. This invention may be implemented in many other ways. The Figures are not necessarily drawn to scale.

DETAILED DESCRIPTION

Time Resolution/Depth Resolution

In illustrative implementations of this invention, the light sensor has an ultrafast time resolution.

In illustrative implementations, this time resolution is so fast that it allows the light sensor to take separate measurements of reflections arriving from different reflectors at different times.

In illustrative implementations, time gating may be employed to achieve the ultrafast time resolution. The time gating may cause the imaging system to take measurements during only very short time windows, and not to take measurements during other periods. The time gating may be achieved in a wide variety of ways, depending on the particular implementation of this invention. For example, in some cases, the time gating is performed by an optoelectronic switch, by a detection pulse, by a periodic timer gate, or in post-processing.

In some implementations, an optoelectronic switch is employed for time gating. The optoelectronic switch may detect an external triggering event and then cause the system to take measurements during a short period of time after the triggering event. Then the system may revert to the "off" state (in which it does not take measurements) until the switch detects another external triggering event. For example, in some cases, an optoelectronic switch may detect an incoming pulse of light, and may cause the system to take measurements during the pulse, and then the system may revert to an "off" state, waiting for the switch to detect the next pulse. Or, for example, the triggering event detected by the switch may be the arrival of light that has a particular phase (corresponding to a particular depth and thus to a particular reflector).

In some implementations, a detection pulse in a THz-TDS spectrometer is employed for time gating. The THz-TDS spectrometer may emit a terahertz pulse to illuminate the sample. A portion of this pulse (called the "detection pulse") may be diverted to an optical delay line and then steered into the detector of the spectrometer. The detection pulse may (due to being delayed in the optical delay line) arrive in the detector at the same time as the reflected pulse from the sample. The arrival of the detection pulse in the detector may trigger the detector to take measurements during an extremely short period of time in which the reflected pulse from the scene is incident at the detector.

In some implementations, the time gating is performed in post-processing. For example, an imaging system may take measurements of light over a period of time, but the system may discard the measurements, unless they occur during a very short time period after a triggering event (that is detected in the measurements) occurs. Again, for example, the triggering event may be a pulse of light or may be a particular phase of light or range of phases of light.

In some implementations, time gating is performed by a periodic timer gate. This gate may—without attempting to detect an external trigger—periodically cause an ultrashort measurement to occur.

In illustrative implementations, the temporal resolution of the imaging system and its depth resolution are equivalent. This is because, in some implementations, the round-trip time (i.e., the amount of time that elapses while light travels from an active light source of imaging system, to a reflector, then back to a light sensor of the system) depends on the depth of the reflector. The better the time resolution of the system, the better its depth resolution.

In some implementations of this invention, the system's depth resolution is so small (and equivalently, its temporal resolution is so fast) that the system can resolve a difference in depth that is much less than $\lambda/(2(NA^2))$, where NA is numerical aperture of the imaging system, and $\lambda$ is wavelength. In contrast, a conventional camera (with a numerical aperture of NA that does not employ time gating) typically cannot—due to the diffraction barrier—achieve a depth resolution less than $\lambda/(2(NA^2))$.

For example, in a prototype of this invention, a THz-TDS imaging system employs time gating, has a numerical aperture of NA≈0.4, and illuminates the sample with light of wavelength of 330 microns. In this prototype, at this wavelength, the depth resolution that is actually achieved by time gating is approximately 150 microns. In contrast, the depth resolution that can be achieved by a conventional camera with the same NA and same $\lambda$, but without time gating, is limited by the diffraction barrier to a distance equal to $\lambda/(2(NA^2))\approx 2$ mm. Thus, in this prototype, due to time gating, the actual depth resolution (about 150 microns) is an order of magnitude smaller than the depth resolution limit (about 2 millimeters) that the diffraction barrier typically imposes on a conventional camera with the same numerical aperture. The prototype described in this paragraph is a non-limiting example of this invention.

To summarize this section: In illustrative implementations, time gating may enable the imaging system to have ultrafast time resolution. This, in turn, may enable the imaging system to take separate measurements of reflections arriving from different reflectors at various times.

Staggered Reflectors Beneath Sample

In illustrative implementations of this invention, an imaging system includes a set of multiple, small reflectors that are located beneath the sample being imaged.

For example, in some cases, the reflectors comprise an array of reflectors (e.g., a 2×2, 3×3, 4×4, or 5×5 array). In some cases, the reflectors comprise a closed-packed (in the x and y dimensions) set of circular reflectors. In some other cases, the reflectors comprise a tesselated (in the x and y dimensions) set of reflectors.

In illustrative implementations, the reflectors (in the set of reflectors beneath the sample) are staggered in depth, with each reflector being at a different depth. For example, in some cases, each reflector is shifted (in the z dimension) from each of its neighbor(s) by a z-distance of a few hundred microns.

Each reflector (beneath the sample) may have a very small cross-section. For example, in some prototypes of this invention, each reflector is circular and has a diameter of 220 µm or 440 µm.

In illustrative implementations, the reflectors are good reflectors in the frequency range of light that illuminates the sample. For example, in some cases, the imaging system includes a THz-TDS spectrometer, and the reflectors have a high reflectivity for terahertz light. Likewise, in some cases, the imaging system performs OCT with infrared light, and the reflectors have a high reflectivity in the infrared range. Or, in some cases, the imaging system performs OCT with light in the visual spectrum, and the reflectors are highly reflective in that spectrum.

In some cases, the reflectors may comprise metal, such as copper, aluminum, silver, zinc, or an alloy (e.g., brass) of one or more of them. Alternatively, or in addition, the reflectors may in some cases include resonant nanostructures to improve reflectivity.

In some cases, each reflector is a flat reflective surface at the top of an elongated structure. For example, the elongated structure may comprise a small wire, small pin, or nanopillar.

In some embodiments of this invention, the imaging system is configured in such a way that, when viewed in a top view, each reflector in the set appears to be partially or entirely inside the beam waist of the light beam that illuminates the sample being imaged. Thus, in some embodiments: (a) a set of points in each reflector have the same (x, y) coordinates as those of points in the beam waist; and (b) each reflector is partially or entirely located (in the x and y dimensions) inside the beam waist.

FIG. 1A shows a perspective view of a 2×2 array of reflectors, in an illustrative implementation of this invention. In the example shown in FIG. 1A, four reflectors (101, 102, 103, 104) are positioned beneath a sample that is being imaged (the sample is not shown in FIG. 1A).

In FIG. 1A, a focused beam of light 121 converges to a circular beam waist. In FIGS. 1A, 1B, 1D, 1E, 1F: (a) the periphery of the beam waist is circle 130; and (b) the beam waist consists of all points inside circle 130 that are in the plane of circle 130. At the beam waist, the width of the light beam is at a local minimum, because the beam is changing from converging to diverging at the beam waist. The outer surface of the beam has an inflection point at the beam waist.

In the example shown in FIG. 1A, the four reflectors are located (in the x and y dimensions) entirely inside the beam waist.

In FIG. 1A, the four reflectors (101, 102, 103, 104) are located at geometric planes 111, 112, 113, 114, respectively. In FIG. 1A, depth increases from right to left. The four reflectors (101, 102, 103, 104) are staggered in depth: reflector 101 is above reflector 102; reflector 102 is above reflector 103; and reflector 103 is above reflector 104.

In FIG. 1A, light wave 132 is emitted by an active light source of the imaging system. Light wave 132 comprises a single pulse (e.g., a pulse of terahertz light emitted by a THz-TDS spectrometer). Light wave 133 comprises light that reflects back from the four reflectors, towards the sample and the detector of the spectrometer. Light wave 133 comprises four pulses that are reflections from the four reflectors (101, 102, 103, 104), respectively. In FIG. 1A, each pulse is shown as a bi-polar pulse to indicate that the single pulse may create a bi-polar pulse in an electrical field in a detector of a THz-TDS spectrometer.

FIGS. 1B-1F each show a top view or side view of reflectors, in illustrative implementations of this invention.

In the examples shown in FIGS. 1A-1J, 2A and 2B, each reflector (e.g., 101, 102, 103, 104, 141, 142, 143, 152, 162, 241, 242, 243, 244, 271, 272, 273, 274) is positioned, relative to the imaging system as a whole and relative to a sample 232, in such a way that light from an active light source of the system passes through sample 232, then reflects from the reflector, then passes through the sample 232 again, and then travels to a light sensor of the system that directly or indirectly measures the light (e.g., by measuring an electric field strength that is proportional to intensity of incident light). The preceding sentence is not intended to be a complete list of all interactions of the light with elements of the system; in many cases, the light interacts with other optical elements of the system (e.g., lens 234, beam splitter 208, a steering mirror, or any other reflective or transmissive optical element of the system). For example, the active light source may comprise terahertz light source 204, and the light sensor may comprise THz-TDS detector 206.

Figure 1B:
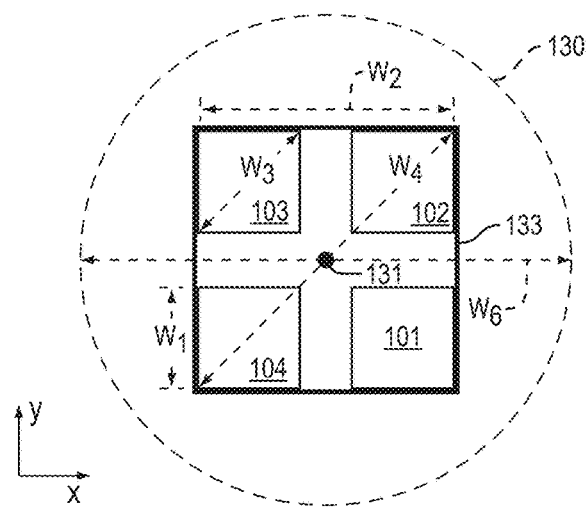
FIGS. 1B, 1D, 1E and 1F each show a top view of a set of reflectors.
Figure 1C:
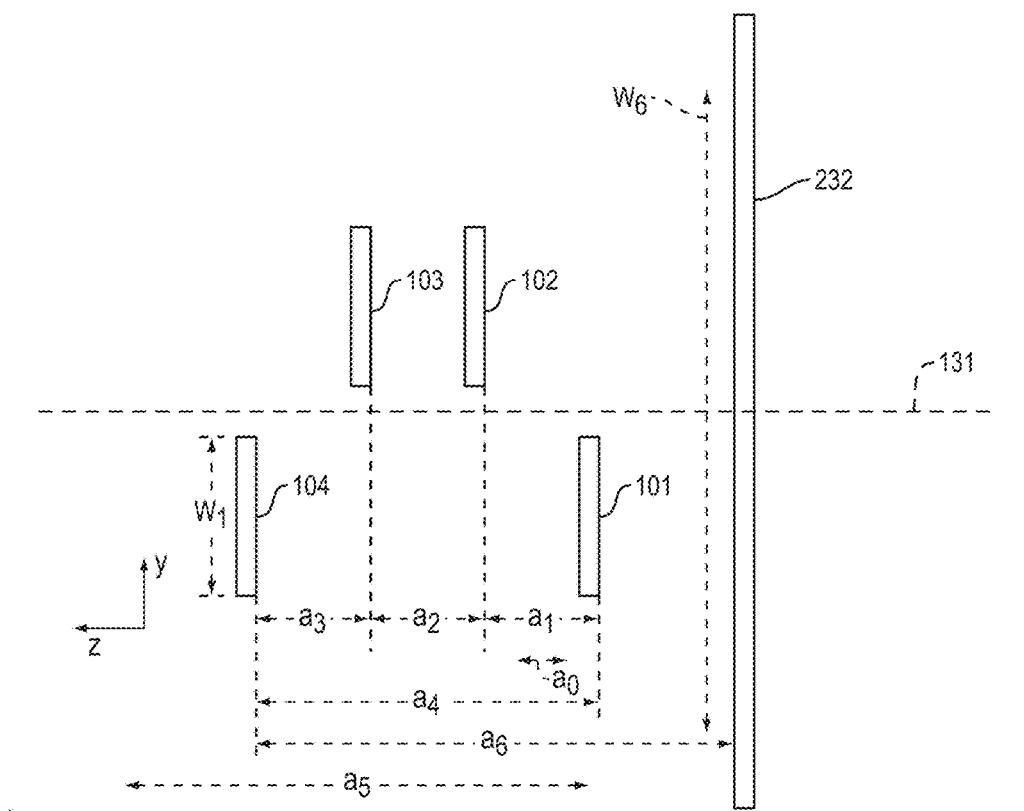
FIG. 1C shows a side view of a set of reflectors.
Figures 1D, 1E:
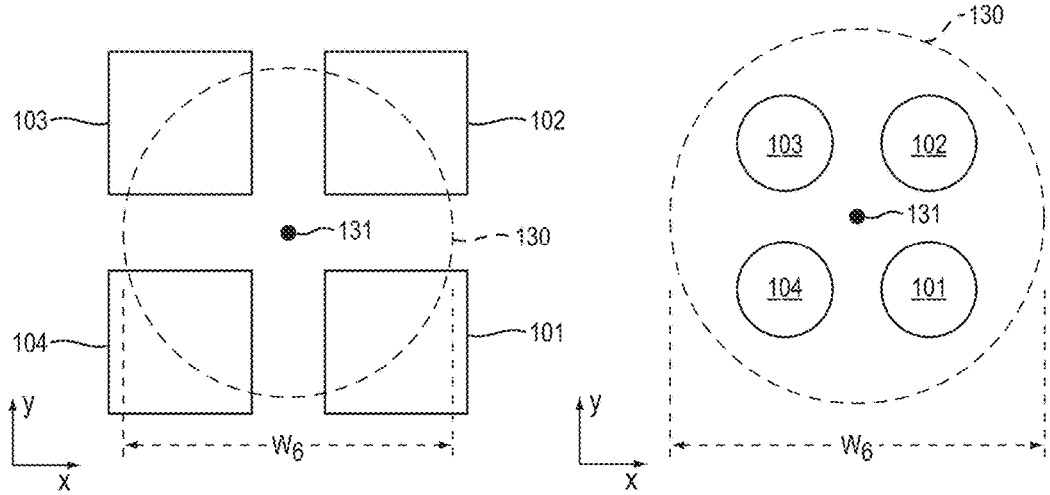

FIGS. 1B and 1E each show a top view of a set of reflectors. These reflectors are rectangular (e.g., square) in FIG. 1B and are circular in FIG. 1E.

In FIGS. 1B and 1E, each reflector 101, 102, 103, 104 in the 2×2 array of reflectors appears—when viewed in top view—to be entirely inside the beam waist. As noted above, circle 130 is the periphery of the beam waist. In FIGS. 1B and 1E, the reflectors 101, 102, 103, 104 are located (in the x and y dimensions) entirely inside the beam waist. In FIGS. 1B and 1E, all points in the reflectors 101, 102, 103, 104 have (x, y) coordinates that are the same as those of points in the beam waist.

In FIGS. 1B-1F, the diameter of the beam waist is distance $w_6$.

FIG. 1C shows a side view of the reflectors shown in FIG. 1A. In FIG. 1C, the optical axis 131 intersects a sample 232. Reflectors 101, 102, 103, 104 are located beneath the sample.

In FIG. 1C: (a) if light were to travel along optical axis 131 from the right to the left side of FIG. 1C, then the light would be moving optically away from an active light source (e.g., 204) that illuminates the sample; and (b) if light were to travel along optical axis 131 from the left to the right side of FIG. 1C, then the light would be moving optically toward a light sensor (e.g., THz-TDS detector 206) of the imaging system.

As used herein, to say that two reflectors are "z-neighbors" or are "z-neighboring" means that they are neighbors in the z-dimension. For example, in FIG. 1C, reflector 104 has only one z-neighbor: specifically, reflector 103. Reflector 103 has only two z-neighbors: specifically, reflectors 104 and 102. Reflector 102 has only two z-neighbors: specifically, reflectors 103 and 101. Reflector 101 has only one z-neighbor that is a reflector: specifically, reflector 102.

In FIG. 1C, the z-distance between reflectors 101 and 102 is distance $a_1$. The z-distance between reflectors 102 and 103 is distance $a_2$. The z-distance between reflectors 103 and 104 is distance $a_3$.

In FIG. 1C, the sum of the z-distances between z-neighbors is $a_4$; that is $a_4 = a_1 + a_2 + a_3$.

In many cases, the reflectors are flat and specular.

However, each reflector diffracts light when it reflects light. In many cases, a reflector is sufficiently small that the effects of this diffraction are significant, causing the light that reflects from the reflector to diverge significantly.

In illustrative implementations, it is desirable to prevent light (that diffracts when it reflects from a reflector) from diverging too far (in the x and y dimensions). To prevent this, in some cases, the sum of the z-distances (e.g., sum $a_4$) between z-neighboring reflectors is less than $d/(2 \tan(\emptyset))$, where d is the diameter $w_6$ of the beam waist, and where $\emptyset$ is the divergence angle of light that reflects (and thus diffracts) from the lowest reflector. In FIG. 1C, distance $a_5$ is equal to $d/(2 \tan(\emptyset))$.

In many cases, the distance between the sample and the reflector that is farthest away from the sample is much less than $\lambda/(2(NA^2))$, where NA is numerical aperture of the imaging system, and $\lambda$ is wavelength. (As noted above, $\lambda/(2(NA^2))$ is a limit on the depth resolution that can be typically be achieved by a conventional camera without time gating). For example, in FIG. 1C, distance $a_6$ is the distance between sample 232 and reflector 104 (the reflector which is farthest from the sample). In the example shown in FIG. 1C, distance $a_6$ is much less than $\lambda/(2(NA^2))$.

As noted above, in illustrative implementations, light reflecting from different reflectors arrives at a light sensor (e.g., a detector of a THz-TD spectrometer) at different times. In many cases, this difference in time-of-arrival is because: (a) the reflectors are staggered in depth, each reflector being at a different depth; and thus (b) the round-trip distance is different for each reflector. As used herein, "round-trip" distance for a reflector means the total distance that light travels, in a path from the active light source of the system to the reflector and then to a light sensor of the system.

In illustrative implementations, the imaging system produces a super-resolved image of a sample, by extracting x, y spatial information from time-resolved data regarding reflected light that reaches the sensor at different times due to different depths of the reflectors.

Thus, in illustrative implementations, it is desirable for the system to be able to temporally resolve light that reflects from different reflectors and arrives at the imaging sensor at different times.

In many cases, the z-distance between each pair of z-neighboring reflectors, respectively, is greater than half the coherence length of light illuminating the sample. For example, in FIG. 1C: (a) distance $a_0$ is equal to the half the coherence length; and (b) distances $a_1$, $a_2$, and $a_3$ are each greater than distance $a_0$.

Furthermore, in many cases, in order to achieve this time resolution, the z-distance between each pair of z-neighboring reflectors, respectively, is greater than the system's time resolution distance. For example, in FIG. 1C, z-distances $a_1$, $a_2$, and $a_3$ are each greater than the system's time resolution distance. As used herein, "time resolution distance" of an imaging system means the distance that light travels during a period of time, which period is equal to the smallest interval of time for which the system can temporally resolve between two pulses of light.

In many implementations, the reflectors (e.g., 101, 102, 103, 104) beneath the sample all have the same size, shape, albedo and other reflective properties.

Alternatively, in some cases, one or more of these factors (size, shape, albedo or other reflective property) is not the same for all of the reflectors beneath the sample. For example, in some cases, one or more of these factors (size, shape, albedo or other reflective property) is varied in such a way that the relative intensity of light reflected from a given reflector is increased. For example, in some cases, it may be desirable to increase the relative intensity of light reflected by reflectors that are at a greater distance from the sample. Likewise, in some cases, if there are a large number of reflectors in the array, it may be desirable to increase the relative intensity of light reflected by reflectors that are located (in the x and y dimensions) closer to the periphery of the array. For example, the relative intensity of light that reflects from a given reflector may be increased by increasing its relative size, or by increasing its relative albedo. In this paragraph: (a) "relative" means relative to other reflectors in the array; and (b) thus, for example, relative albedo of a given reflector means the albedo of the given reflector, relative to the albedo of the other reflectors in the array.

Figure 1F:
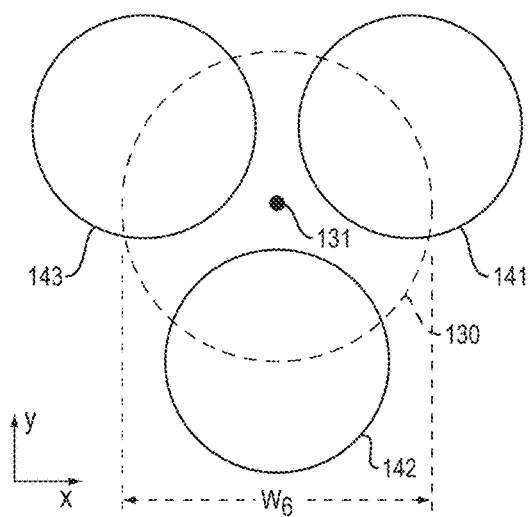

FIGS. 1D and 1F each show a top view of a set of reflectors. These reflectors are rectangular (e.g., square) in FIG. 1D and are circular in FIG. 1F.

In FIGS. 1D and 1F, each reflector in the set of reflectors (e.g., 101, 102, 103 and 104, or 141, 142, 143) appears—when viewed in top view—to be only partially inside the beam waist. As noted above, circle 130 is the periphery of the beam waist. Thus, in FIGS. 1D and 1F, each reflector 101, 102, 103, 104, 141, 142, 143 is located (in the x and y dimensions) only partially inside the beam waist. In FIGS. 1D and 1F, only a subset of points in each reflector 101, 102, 103, 104, 141, 142, 143 have (x, y) coordinates that are the same as those of points in the beam waist.

Figure 1G:
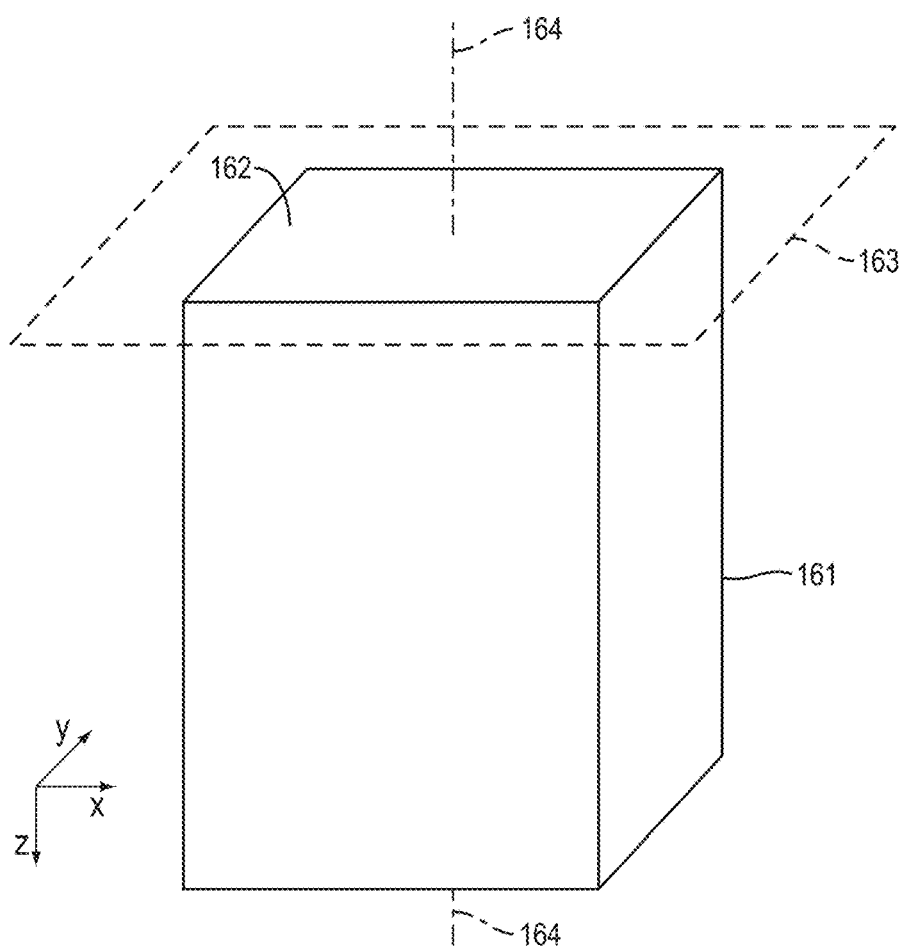
FIGS. 1G and 1I each show a reflector that comprises a flat end of an elongated structure.
Figure 1H:
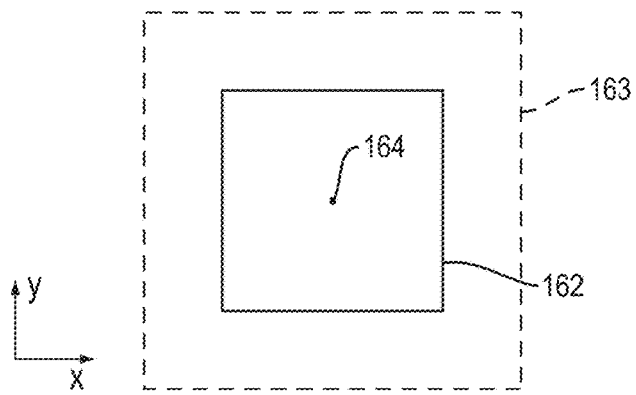
FIGS. 1H and 1J show cross-sectional views of the elongated structures in FIGS. 1G and 1I, respectively.
Figure 1I:
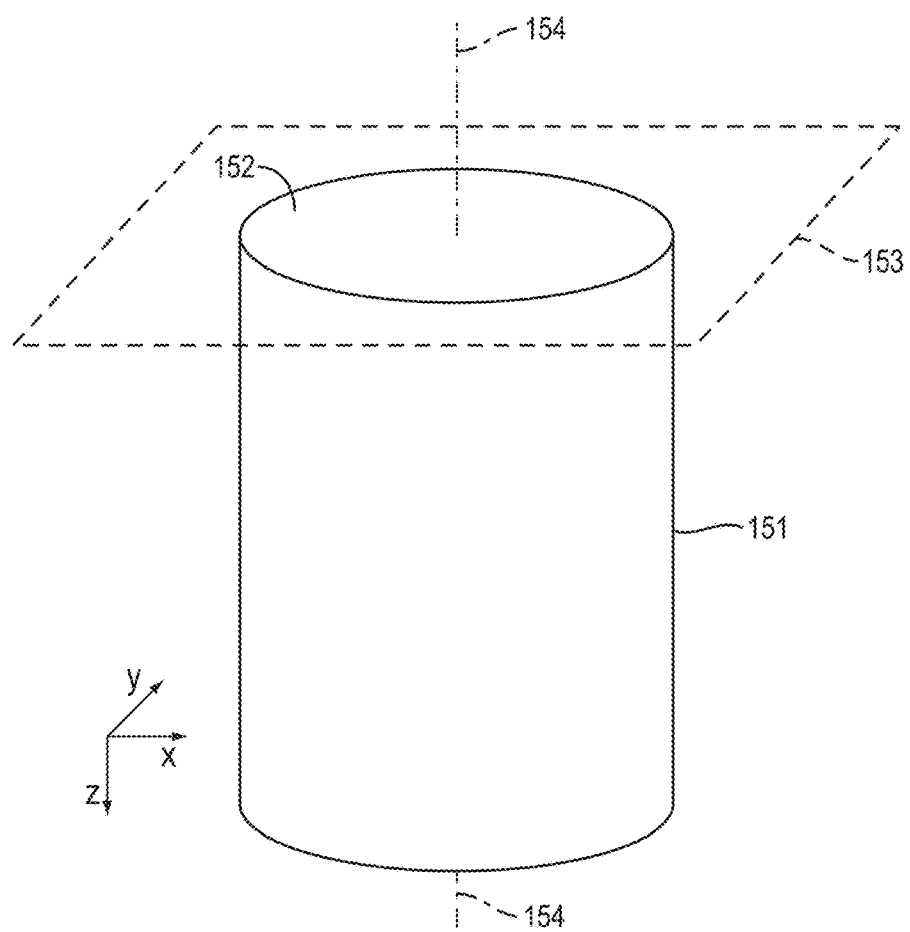

FIGS. 1G and 1I each show a reflector that comprises a flat end of an elongated structure, in illustrative implementations of this invention. The elongated structure (161, 151) has a rectangular cross-section in FIG. 1G and a circular cross-section in FIG. 1I.

In the examples shown in FIGS. 1G and 1I: (a) a reflector 152, 162 comprises a flat, specular, reflective surface; (b) the elongated structure 151, 161 has a longitudinal axis 154, 164; (c) the reflector 152, 162 is located at a longitudinal end of the elongated structure 151, 152; and (d) the elongated structure 151, 161 has an aspect ratio of 1:x, where x is a finite number greater than or equal to 2.

Figure 1J:
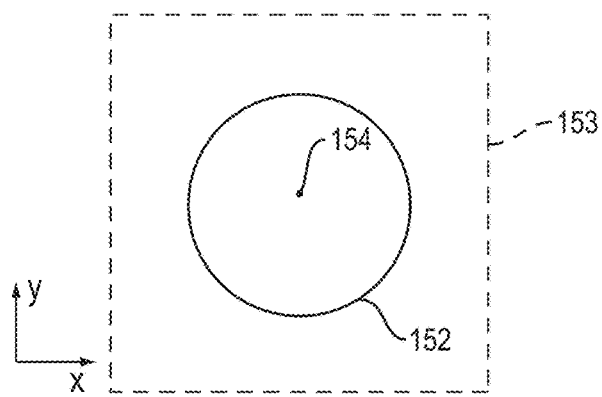

FIGS. 1H and 1J show cross-sectional views of the elongated structures in FIGS. 1G and 1I, respectively. The cross-section for FIGS. 1H and 1J is taken in a cross-sectional plane 153, 163 which: (a) is perpendicular to the longitudinal axis 154, 164 of the structure 151, 161; and (b) is coplanar with the flat surface of the reflector 152, 162.

This invention is not limited to square, rectangular or circular reflectors. In illustrative implementations, a reflector may have any 2D or 3D shape, and may comprise a surface on a structure that has any cross-sectional shape.

In many implementations, the set of reflectors beneath the sample (and each reflector in the set) are small relative to the diameter of beam waist and relative to the wavelength of light illuminating the sample.

In many cases, this small size is desirable, to ensure that the set of reflectors (which are staggered in depth and thus reflect light at different times) occupy a sufficiently small region that the reflected light from the reflectors encodes (in time) data from which a super-resolved image of the sample may be extracted.

The following discussion gives examples of small sizes, in some implementations of this invention. However, before discussing these non-limiting examples of small size, it is helpful to first define "maximum dimension" and "convex hull".

As used herein, the "maximum dimension" of an object means the longest distance between any two points of the object. For example, the maximum dimension of a circle is the diameter of the circle. Also, for example, if the sides of a square each have length A, then the maximum dimension of the square is $\sqrt{2}A$ (the length of the diagonal between two opposite vertices of the square).

As used herein, the term "convex hull" is used in its mathematical sense. For example, a convex hull of a set Q of points in a Euclidean plane is the smallest convex set that contains Q. Also, for example, in FIG. 1C, the region enclosed by line 133 is the convex hull of the four rectangles 101, 102, 103, 104.

Now that we have these definitions, we list some non-limiting examples of small sizes of the set of reflectors (or of each reflector).

In some cases, the maximum dimension (e.g., $w_4$ in FIG. 1C) of the convex hull of the set of the reflectors is less than the diameter of the beam waist.

In some cases, the maximum dimension (e.g., $w_4$ in FIG. 1C) of the convex hull of the set of the reflectors is less than the wavelength of the maximum intensity frequency component of light illuminating the sample.

In some cases: (a) the set of reflectors comprises a "rectangular grid" array of reflectors; and (b) the length of the longest straight line segment along any side of the array (e.g., $w_2$ in FIG. 1C) is less than the diameter of the beam waist.

In some cases: (a) the set of reflectors comprises a "rectangular grid" array of reflectors; and (b) the length of the longest straight line segment along any side of the array (e.g., $w_2$ in FIG. 1C) is less than the wavelength of the maximum intensity frequency component of light illuminating the sample.

In some cases, the maximum dimension (e.g., $w_3$ in FIG. 1C) of each reflector in the set, respectively, is less than 1/R times the diameter of the beam waist, where R is any number greater than or equal to 1.5.

In some cases, the maximum dimension (e.g., $w_3$ in FIG. 1C) of each reflector in the set, respectively, is less than 1/R times the wavelength of the maximum intensity frequency component of light illuminating the sample, where R is any number greater than or equal to 1.5.

In some cases: (a) each reflector in the set is a polygon; and (b) the length of the longest straight line segment of a side of the polygon (e.g., $w_1$ in FIG. 1C) is less than 1/R times the diameter of the beam waist, where R is any number greater than or equal to 1.5.

In some cases: (a) each reflector in the set is a polygon; and (b) the length of the longest straight line segment of a side of the polygon (e.g., $w_1$ in FIG. 1C) is less than 1/R times the wavelength of the maximum intensity frequency component of light illuminating the sample, where R is any number greater than or equal to 1.5.

For purposes of the preceding four paragraphs, non-limiting examples of values of R include 1.5, 2, 2.154, 3, 4, and 5. In some cases, which value of R is desirable for a given implementation of this invention may depend on factors such as the number of reflectors or positioning of the reflectors relative to each other in the x and y dimensions (e.g., array, tessellation, or close-packed). For example, selecting R=2.154 may be appropriate in a case in which the set of reflectors consists of three closed-packed circles (because the smallest circle that encloses three close-packed circles has a radius that is about 2.154 times the radius of each of the close-packed circles).

For purposes of preceding nine paragraphs: (a) the z-dimension is ignored; (b) each shape is treated as being a 2D shape that exists only in the x and y dimensions; that is, each given shape is treated as being the orthogonal projection of that given shape onto the x-y plane; and (c) all distances are measured in the x and y dimensions only. For example, if the (x,y,z) coordinates of a first point, second point and third point were (0,0,0), (0,1,2), and (1,0,18) respectively, then, for purposes of the preceding nine paragraphs: (a) the first, second and third points would be treated as points in 2D space with (x,y) coordinates of (0,0), (0,1) and (1,0), respectively; and (b) the distance between the first and third points would be treated as 1 (not $\sqrt{1^2+18^2}$).

This invention is not limited to any particular number of reflectors. For example, the set of reflectors beneath the sample may consist of: (a) three reflectors (e.g., three close-packed circular reflectors); (b) four reflectors (e.g., a 2×2 array of reflectors); (c) seven reflectors (e.g., seven circular reflectors that are close-packed so that six reflectors are arranged in a circle around a central reflector); (d) nine reflectors (e.g., in a 3×3 array); (e) sixteen reflectors (e.g., in a 4×4 array); (f) twenty-five reflectors (e.g., in a 5×5 array); or (g) any other number of reflectors.

As noted above, in many cases, the imaging system produces a super-resolved image of a sample, by extracting x, y spatial information from time-resolved data regarding reflected light that reaches the sensor at different times due to different depths of the reflectors.

In illustrative implementations, increasing the number of reflectors (in the set of reflectors beneath the sample) tends to increase the x, y spatial resolution of the super-resolved image. However, increasing the number of reflectors may tend to increase the SNR (signal-to-noise ratio) of the system, because (all other factors being equal) the smaller the area of a reflector, the less light that will be reflected back from the reflector.

As noted above, in some cases: (a) light that reflects from each reflector diverges (e.g., due to diffraction) at a divergence angle; and (b) the sum of z-distances between z-neighboring reflectors may be less than $d/(2 \tan(\emptyset))$, where $d=w_6$ is the diameter of the beam waist and $\emptyset$ is the divergence angle.

In some cases, the reflectors are engineered to decrease the divergence angle. For example, the divergence angle of light reflecting from a reflector may be reduced by: (a) etching the top surface of the reflector with sub-wavelength periodic metallic structures in such as way to create destructive interference at larger angles; (b) fabricating nano-antenna or micro-antenna arrays at the top of the reflector; (c) fabricating a parabolic surface at the top of the reflector; or (d) applying one or more thin layer coatings in such way as to create destructive interference at larger angles.

Decreasing the divergence angle may be desirable, at least in some cases. For example, decreasing the divergence angle may, in turn, allow the sum of the z-distances (between z-neighboring reflectors) to be increased. Increasing the sum of z-distances may, in turn, facilitate increasing the number of reflectors, while keeping the distance of each z-step constant. Or, increasing the sum of the z-distances may be desirable, in order to increase distance of each z-step, which in turn may facilitate employing a time-of-flight sensor that has a slower temporal resolution. With a smaller reflection angle from each reflector, the distance from the entire array and the sample may also be further increased.

THz-TDS Imaging with Staggered Reflectors Beneath Sample

Figure 2A:
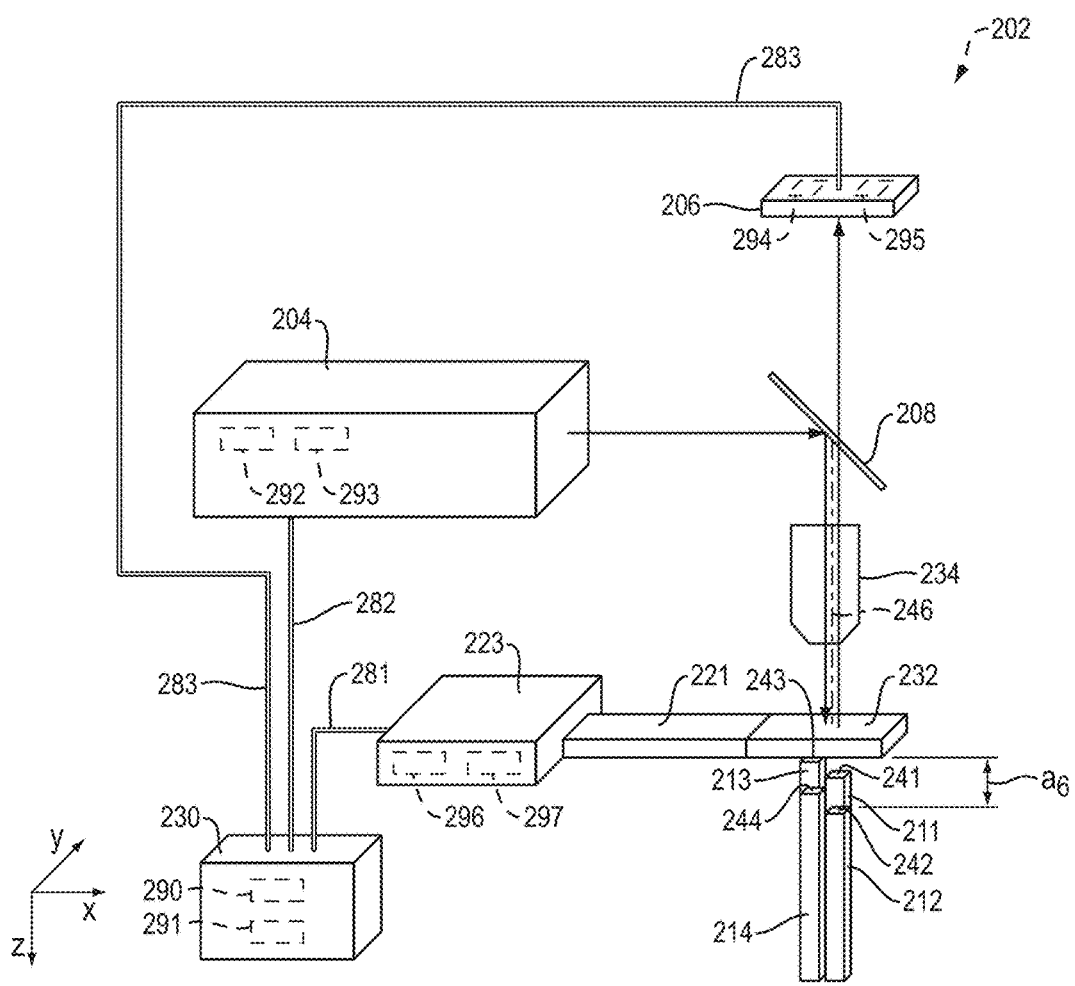
FIG. 2A shows hardware for a THz-TDS imaging system that includes reflectors at staggered depths beneath the sample.

FIG. 2A shows hardware for a THz-TDS imaging system that includes reflectors at staggered depths beneath the sample, in an illustrative implementation of this invention. In the example shown in FIG. 2A, a THz-TDS spectrometer 283 comprises a terahertz light source 204, a beam splitter 208 and a detector 206. Detector 206 may measure incident light by measuring an electric field.

In FIG. 2A, terahertz light source 204 emits ultrashort pulses of terahertz light. Each pulse of terahertz light is emitted by light source 204, then reflected by beam splitter 208, then focused by objective lens 234, then travels through a sample 232, and then is reflected by reflectors 241, 242, 243, 244. Because the four reflectors 241, 242, 243, 244 are at different depths, each pulse of light emitted by light source 204 is reflected back (from the reflectors) as a time sequence of four fainter pulses. These four fainter pulses of reflected light travel through sample 232 again, then are transmitted by beam splitter 208, and then travel to, and are measured by, detector 206 of the THz-TDS system. Thus, in FIG. 2A, the impulse response of the four reflectors to a single pulse of terahertz limit emitted by light source 204 is a time sequence of four fainter pulses that reflect back from the reflectors toward the sample and the THZ-TDS detector.

In addition, some light reflects directly back from sample 232 to detector 206, without ever reaching the reflectors. In illustrative implementations, this light that reflects directly back from the sample (without reaching the reflectors) is not used when generating the super-resolved image of the image.

In FIG. 2A, the reflectors 241, 242, 243, 244 are beneath the sample 232 and are staggered in depth, with each reflector being at a different depth. Furthermore, the reflectors are very small and fit closely together.

In FIG. 2A, objective lens 234 refracts light (from light source 204) in such a way that it forms a beam of light that converges to a focus in a small 3D region of focus that includes reflectors 241, 242, 243, 244 and a portion of sample 232 located above the reflectors. In a plane that is parallel to the x-y plane, the smallest cross-section of this region of focus is a circular focal spot. (In the example shown in FIGS. 1A, 1B, 1D, 1E, 1F, circle 130 is the periphery of the circular focal spot and is also the periphery of the beam waist).

In FIG. 2A, reflectors 241, 242, 243, 244 are located (in the x and y dimensions) entirely within the circular focal spot. Alternatively, in FIG. 2A, reflectors 241, 242, 243, 244 are each located (in the x and y dimensions) only partially within the circular focal spot.

In FIG. 2A, distance $a_6$ is the distance between sample 232 and reflector 242 (the reflector which is farthest from the sample). In the example shown in FIG. 2A, distance $a_6$ is much less than $\lambda/(2(NA^2))$.

In FIG. 2A, the sample is much larger than the circular focal spot. In order to capture an image of the entire sample, the sample may be rastered in the x and y dimensions, thus causing the circular focal spot of light to be positioned at different x, y positions of the sample at different times. An actuated stage includes stage 221 and actuator 223. Stage 221 supports sample 232. Actuator 223 may actuate x and y motion of stage 221 and thus sample 232. Actuator 223 may comprise one or more motors. In FIG. 2A, objective lens 234 and reflectors 241, 242, 243, 244 may remain stationary, relative to the imaging system as a whole, while the sample is rastered in the x and y dimensions.

Alternatively, in some cases, rastering is not performed. For example, in some cases: (a) the sample is smaller than the array of reflectors and is located (in the x and y dimensions) entirely within the circular focal spot; and (b) thus, rastering is avoided. Or, in some cases, an array of detectors may be employed, each focused at a different circular focal spot, and the sample and its stage may remain stationary (instead of being rastered).

Figure 9:
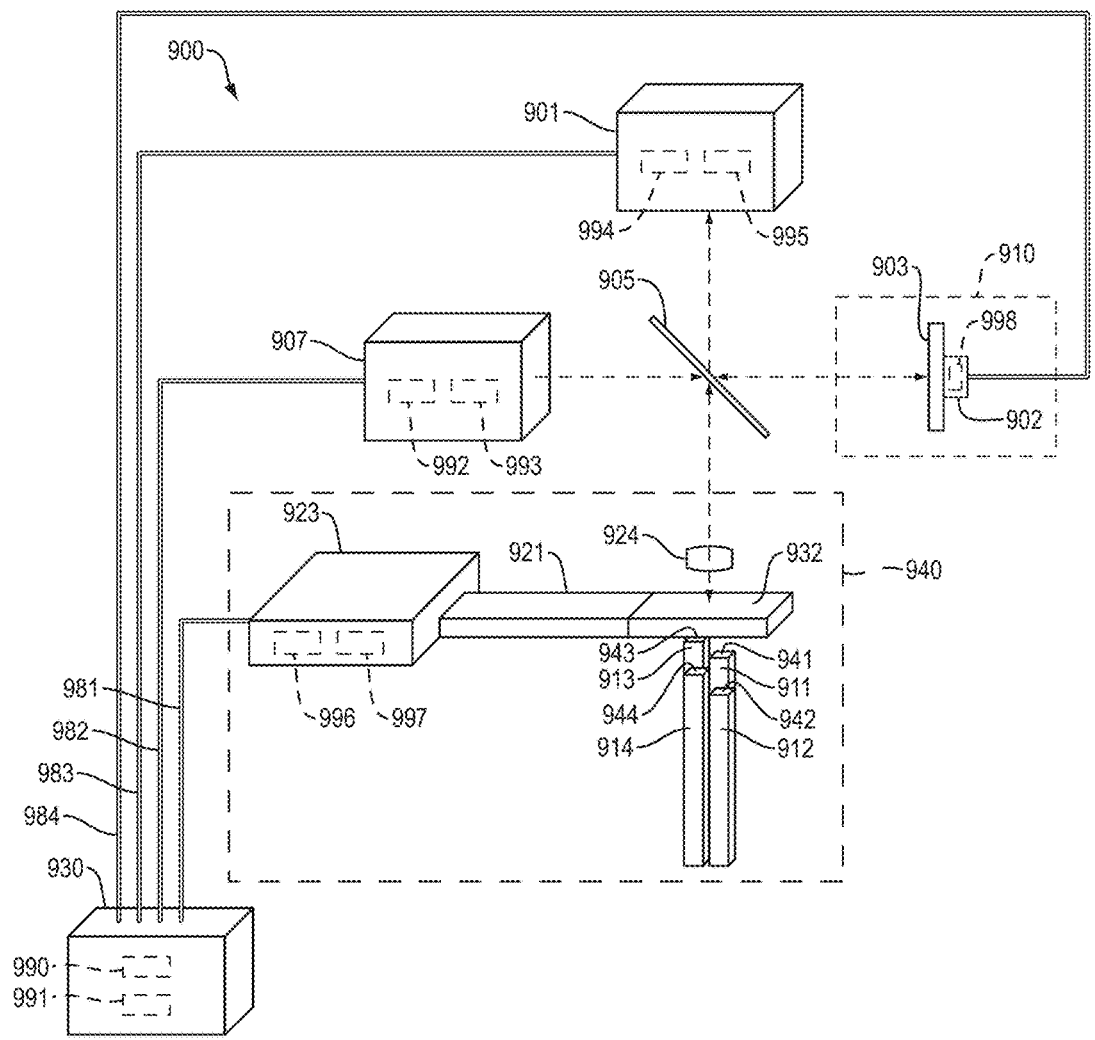
FIG. 9 shows hardware for an OCT imaging system that includes reflectors staggered at different depths beneath the sample.

In FIGS. 2A and 9, stage 221, 921 may support sample 232, 932 directly, or may indirectly support the sample by supporting a transparent object (e.g., a slide) to which the sample 232, 932 is attached. For example, in some cases: (a) sample 232, 932 is attached to a transparent slide; stage 221, 921 includes a circular hole; (b) the sample and slide may be positioned in such a way that a portion of the sample is above the circular hole, allowing light to pass through the circular hole, slide and sample; (c) edges of the slide may extend beyond the circular hole and be supported by the stage; and (d) the stage may include arms, clips or other devices that hold the slide in position while the sample is being imaged.

In FIG. 2A, a computer 230 may control and interface with microcontrollers 292, 294, 296, which in turn may control and interface with light source 204, light sensor 206, and actuator 223, respectively. The computer 230 may output instructions that cause the light source, light sensor and actuated stage to operate in a synchronized manner. For example, the computer 230 may output instructions that cause the actuated stage to raster the sample to a new x, y position, and then cause the light source to emit a light pulse and the light sensor to capture an image, while the sample is in this new x, y position. Computer 230 may store data in, and access data from, memory device 290. In FIG. 2A, devices in the imaging system may communicate with each other via a set of wires (e.g., 281, 282, 283). Alternatively, in some cases, devices in the imaging system may employ wireless modules (e.g., 291, 293, 295) to communicate with each other by wireless communication.

In FIG. 2A, sample 232 is translucent, in the frequency range of light that illuminates the sample. For example, in some cases, sample 232 is translucent to, and illuminated by, terahertz light. Preferably, sample 232 is thin in the z-dimension (e.g., has a thickness less than ten times the wavelength of light illuminating the sample). This tends to reduce interreflections within the sample and to increase transmission of light through the sample.

Figure 2B:
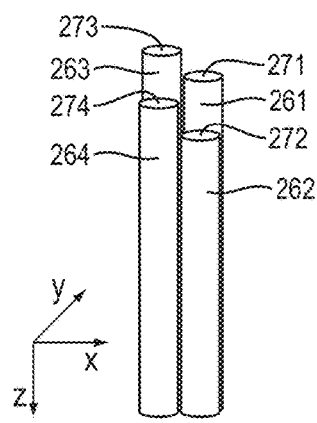
FIG. 2B shows reflectors that have a circular cross-section.

In FIGS. 2A and 2B, reflectors 241, 242, 243, 244, 271, 272, 273, 274 comprise flat reflective surfaces at the longitudinal ends of elongated structures 211, 212, 213, 214, 261, 262, 263, 264, respectively. Elongated structures 211, 212, 213, 214, 261, 262, 263, 264 may, for example, comprise wires, pins or nanopillars, and may, in some cases, be covered with resonant structures to increase reflectivity.

In some cases, the flat reflective surface of the reflectors is produced by ablation of a tip of an elongated structure, or by physically cutting an elongated structure into two parts.

In some cases, it is desirable for the elongated structures (and thus reflectors) to have a square or rectangular cross-section. This is because a square or rectangular cross-section facilitates a high packing density of reflectors in a "grid" array. However, in many cases, it is easier to fabricate elongated structures (and thus reflectors) that have a circular cross-section. The elongated structures (and the reflectors) have a square cross-section in FIG. 2A and a circular cross-section in FIG. 2B.

This invention is not limited to the hardware shown in FIG. 2A. Any type of THz-TDS spectrometer may be employed, in illustrative implementations of this invention. For example, in some cases, the THz-TDS spectrometer operates in transmission mode or detection mode, and detects returning terahertz radiation by photoconductive antennas or nonlinear crystals.

In illustrative implementations of this invention, the THz-TDS spectrometer may generate terahertz radiation in a variety of different ways. For example, a photoconductive emitter (sometimes called photoconductive switch) may emit pulsed terahertz radiation. The photoconductive emitter may include a laser (e.g., a mode-locked fiber laser, or a Ti-Sapphire laser) and biased antenna electrodes patterned in a semi-conductor material. The laser may emit an ultrashort laser pulse that causes a sudden electric current to flow across these electrodes, which in turn causes a pulse of terahertz radiation to be emitted. Or, for example, the THz-TDS spectrometer may employ optical rectification. In the optical rectification, an ultrashort laser pulse (e.g., emitted by an amplified Ti-Sapphire laser) may pass through a transparent crystal, causing a pulse of terahertz radiation to be emitted.

In illustrative implementations of this invention, the THz-TDS spectrometer may detect a pulse of incident terahertz light (that is returning from the sample being imaged). For example, a detection pulse (which is a portion of the laser pulse that triggered the terahertz radiation) may be steered into a detector. In the detector, the electric field of the terahertz pulse (that reflects from the scene) may interact with the much shorter detection pulse, producing an electrical signal that is proportional to the electric field of the terahertz pulse. By repeating this process (and by using an optical delay line to vary the timing of the detection pulse in different repetitions), different frequencies in the terahertz pulse may be scanned and the electric field of the terahertz pulse as a function of time may be determined. Then a Fourier transform may be performed on this time-domain signal, to calculate a frequency spectrum.

In illustrative implementations of this invention, the THZ-TDS spectrometer may detect the terahertz radiation (that returns from the sample being imaged) in a variety of different ways. For example, antennas used in photoconductive generation of the terahertz radiation may be employed to detect the returning terahertz radiation, by photoconductive detection. In this approach, the returning terahertz radiation may drive electric current across the antenna leads, and an amplifier may amplify this current. The amplified current may correspond to the field strength of the returning terahertz radiation. Or, for example, the crystals used for optical rectification generation of the terahertz radiation may be employed for detecting the returning terahertz radiation. The crystals may be birefringent in an electric field, causing a change in polarization of the terahertz radiation that is proportional to the electric field strength. This change in polarization may be measured.

In some implementations: the detector (e.g. 206) of the THz-TDS spectrometer measures incident terahertz light by measuring an electric field, and thus the detector (e.g., 206) is an example of a light sensor. Other types of light sensors may be employed in this invention.

In illustrative implementations, either terahertz time-domain spectroscopy (THz-TDS) or optical coherence tomography (OCT) may be employed. An advantage of employing a THz-TDS spectrometer is that the detection process in THz-TDS may be based on electric field measurements with ultrafast (e.g., femtosecond) time steps, which are more directly accessible measurements than autocorrelation which may be used in OCT.

The following six paragraphs describe a prototype of this invention.

In this prototype, a THz time domain spectrometer includes a fiber-coupled laser and photoconductive switches. An objective lens comprises an HDPE (high-density polyethylene) lens with 5 cm focal length. This lens focuses THz light from the spectrometer onto a 2×2 array of reflectors, creating a focal spot between 500 um and 1 mm in diameter.

In this prototype, the reflectors are packed closely together, and have a diameter of 220 μm each (or 440 μm each). The reflectors are copper or brass wires with polished tips to reflect the THz light back.

In this prototype, the reflectors are positioned at different depths, and thus reflect a pulse of light at different times relative to each other. These time-gated reflections enable time-encoding of information from which super-resolved image may be extracted.

In this prototype, the sample has thickness (300 μm) that is comparable to the wavelength of the incident light.

In this prototype, the emitted THz light is focused on to the sample with a high-density-polyethylene HDPE lens of numerical aperture NA, diameter D, focal length f, and imaging medium refractive index of n, where (NA=nD/2f=1×25/2×3≈0.4). In this prototype, the reflectors are at the ends of pins in a 2×2 metallic pin array.

In this prototype, the diameter of each reflector is 220 μm or 440 μm diameters, and each reflector is shifted in z by a few hundred microns relative to its neighbor(s) in the z dimension.

The prototype described in the preceding six paragraphs is a non-limiting example. This invention may be implemented in many other ways.

FIGS. 3A, 3B, 3C, 4A, 4B, 4C, 4D, 4E are images of reflected light, in illustrative implementations of this invention.

Figure 3A:
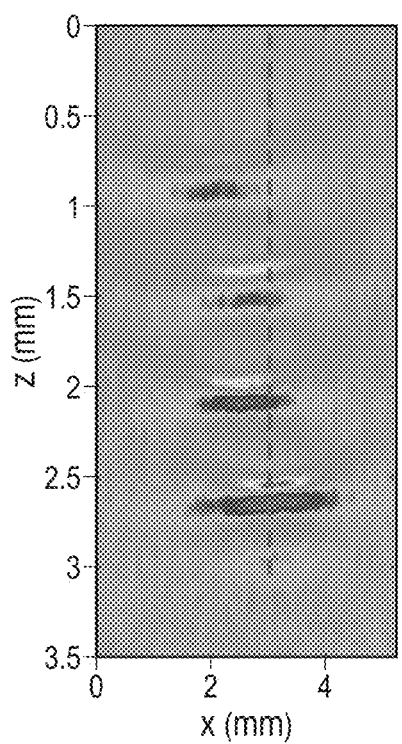
FIGS. 3A and 3B are images of light reflecting from reflectors.
Figure 3B:
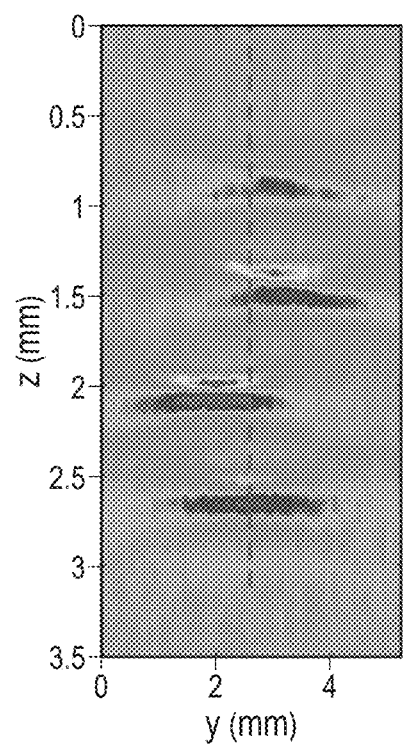

FIGS. 3A and 3B show light reflecting from four reflectors at an arbitrary x, y point. In FIGS. 3A and 3B, the arbitrary x, y point is x=2.5 mm and y=2.4 mm. (The vertical dashed lines in FIGS. 3A and 3B are at x=2.5 mm and y=2.4 mm, respectively.)

FIGS. 3A and 3B are x-z and y-z images, respectively. Thus, in FIGS. 3A and 3B, the vertical axis is the z dimension. Different coordinates along the z axis of FIGS. 3A and 3B correspond to different depths of the reflectors. Different coordinates along the z-axis in FIGS. 3A and 3B also correspond to different times-of-arrival (at the THZ-TDS detector) of light that reflected from the reflectors. This is because the round-trip distance that light travels to and from a given reflector—and the amount of time it takes for light to traverse the round-trip distance—is different depending on the depth of the given reflector. Thus: (a) in FIGS. 3A and 3B, the vertical axis is equivalent to time-of-arrival of light; and (b) the x-z and y-z images are equivalent to x-t and y-t images, respectively. (In an x-t or y-t image, the vertical axis is time.)

In FIGS. 3A and 3B, the image shows four bi-polar pulses of electric field strength measured by a THz-TDS spectrometer. These four bi-polar pulses arrive at the detector of the THz-TDS spectrometer at different times, each from a different reflector at a different depth. Thus, these four pulses are shown in different positions on the z-axis, because different positions on the z-axis correspond to different depths of the reflectors and thus to different times-of-arrival of light. In FIGS. 3A and 3B, the first, second, third and fourth bi-polar pulses are located (in the z-dimension) at approximately 2.4-2.5 mm, 2.0-2.1 mm, 1.4-1.5 mm, and 0.8-0.9 mm, respectively.

In the example shown in FIGS. 3A and 3B, each bi-polar pulse is smeared in the horizontal (x or y dimension) and is not smeared in the vertical (depth or time) dimension. This is because light may diffract (and thus diverge) when it reflects from the reflectors. Thus, a diverging beam of light may reflect from each reflector, and the divergence (in the x and y dimensions) may cause the smearing in the horizontal dimension of x-z and y-z images shown in FIGS. 3A and 3B. In many implementations, the reflectors themselves do not overlap in the x and y dimensions, even though diverging reflections of light from the reflectors overlap in (in the x or y dimension) in images captured by a THz-TDS spectrometer.

In FIGS. 3A and 3B, the four bi-polar pulses of light are the impulse response of the four reflectors to a single pulse of terahertz light emitted by a THz-TDS spectrometer. This single pulse travels from the spectrometer, through the sample, and to the respective reflectors, which reflect it back as four separate pulses due to the different depths of the reflectors (a separate pulse for each reflector). These four reflected pulses then travel pass through the sample and travel to the spectrometer.

In some implementations: (a), a thin sample is inserted above the reflectors; and (b) the direct reflection from the sample itself is stronger than the signal from the reflectors. Although this reflection from the sample is separable in time, it notably reduces the signal that reaches the reflectors and comes back to the light sensor of the system (e.g., a detector of a THz-TDS spectrometer).

Figures 3C, 3D:
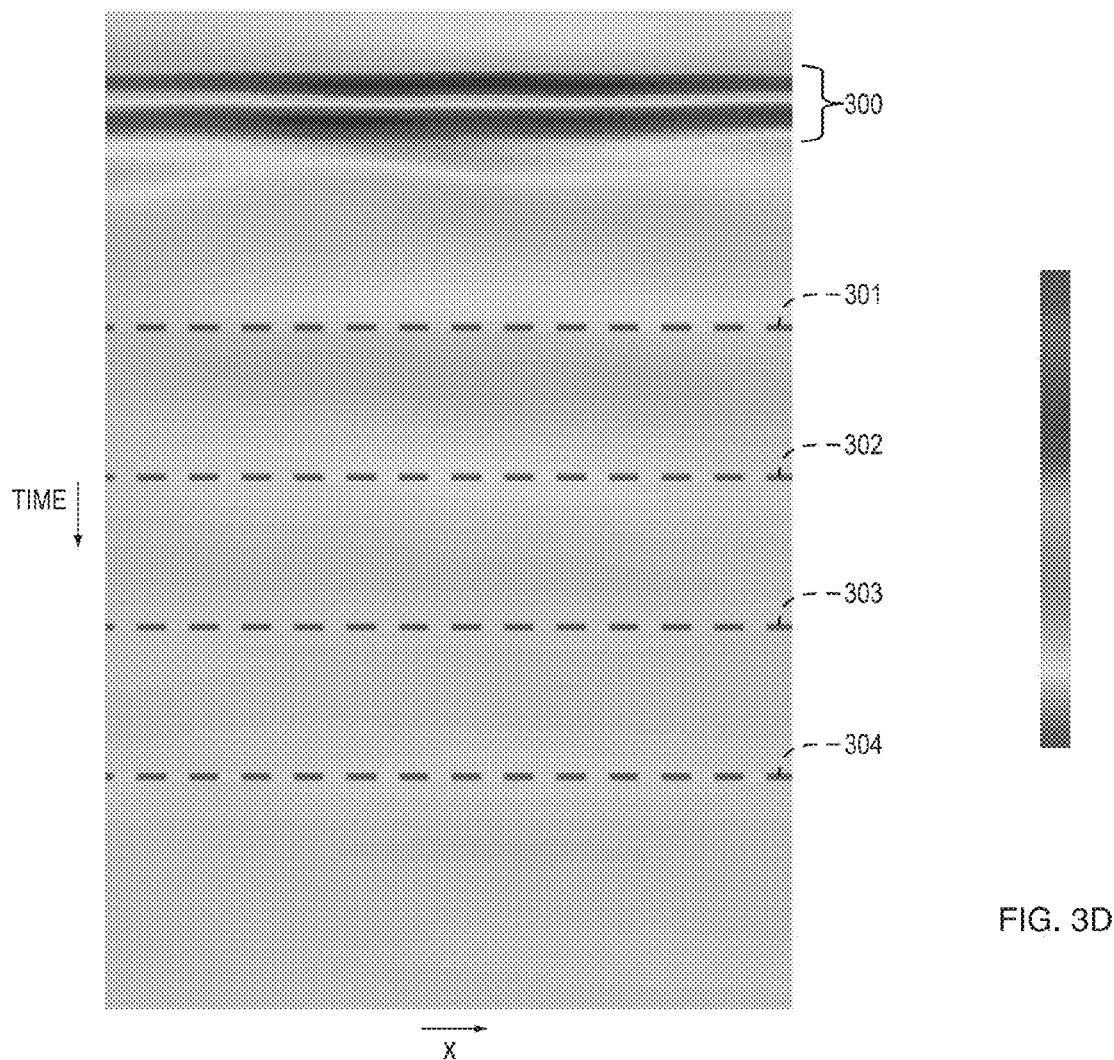
FIG. 3C is an image of light reflecting from a sample and four reflectors.
FIG. 3D shows an HSV color map that is employed in FIGS. 3A-3C.

FIG. 3C shows a x-t image of light that reflected from a sample and from four reflectors. In FIG. 3C, the vertical axis is time (specifically, time of arrival of light at the detector of a THz-TDS spectrometer).

In FIG. 3C, a bi-polar pulse of light that reflected directly from the sample is recorded as two prominent horizontal smears in vertical region 300 of the image. In FIG. 3C, four fainter bi-polar pulses also reflected from the four reflectors, respectively. In FIG. 3C, these four pulses are centered (in the time dimension) at dashed lines 301, 302, 303, 304, respectively. In FIG. 3C, each bi-polar pulse from a reflector appears as a pair of faint horizontal smears.

In FIG. 3C, the five bi-polar pulses of light (one from the sample and four from the four reflectors) are the impulse response of the sample and four reflectors to a single pulse of terahertz light emitted by a THz-TDS spectrometer. The five pulses (reflected from the sample and four reflectors, respectively) arrive at a detector of the THz-TDS spectrometer at different times, because of the different depths of the reflectors.

In illustrative implementations, the light sensor (e.g., a detector of a THz-TDS spectrometer) captures information about incident radiation at each x, y pixel at different times. Thus, the light sensor may capture data that comprises an x-y-t data cube. For example, FIGS. 3A, 3B and 3C represent planar "slices" of an x-y-t data cube (or, equivalently, x-y-z data cube). In FIG. 3A, the slice is an x-z (or equivalently, x-t) plane. In FIG. 3B, the slice is a y-z (or equivalently, y-t) plane. In FIG. 3C, the slice is an x-t (or equivalently, x-z) plane.

FIG. 3D shows an HSV (hue, saturation, value) color map that is employed in FIGS. 3A, 3B and 3C. The normalized electric field strength (normalized to the value of the positive peak of the bipolar THz electric field pulse) measured by the THz-TDS spectrometer may range between −1 and +1. Different colors in this HSV color map correspond to different values of the normalized electric field strength. Specifically: (a) the higher (vertically) a given color is in the HSV color map shown in FIG. 3D, the closer the electric field strength that the given color represents is to +1; and (b) the lower (vertically) a specific color is in the HSV color map shown in FIG. 3D, the closer the electric field strength that the specific color represents is to −1. Thus, in this HSV color map, dark blue represents a positive electric field strength.

FIGS. 4A, 4B, 4C, and 4D are x-y images of light reflecting from a first reflector, second reflector, third reflector and fourth reflector, respectively. Each of these images were taken at different times. Specifically, FIGS. 4A, 4B, 4C, and 4D were captured when light from the first, second, third and fourth reflectors, respectively, reached the THz-TDS detector. In the example shown in FIGS. 4A-4D, these times-of-arrival are different, because the reflectors are at different depths, and thus the amount of time that light takes to travel from the THz-TDS spectrometer to the reflector and back to the spectrometer) is different for each reflector. In each of these four images (FIGS. 4A-4D), the star * marks the peak (in the x and y dimensions) of intensity of the reflection and thus indicates the location (in the x and y dimensions) of the center of the reflector.

Figure 4A:
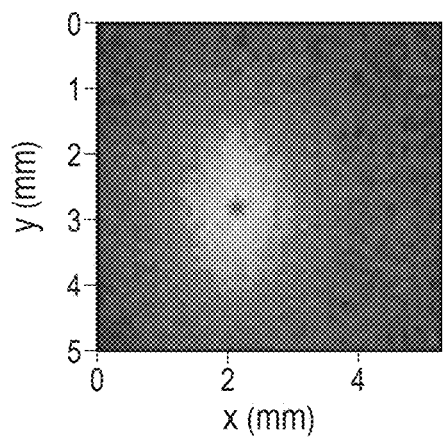
FIGS. 4A, 4B, 4C, and 4D are x-y images of light reflecting from four different reflectors, respectively.
Figure 4B:
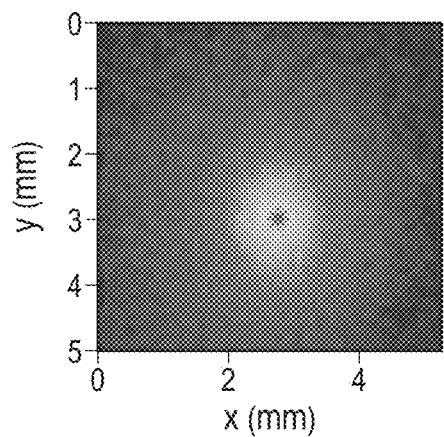
Figure 4C:
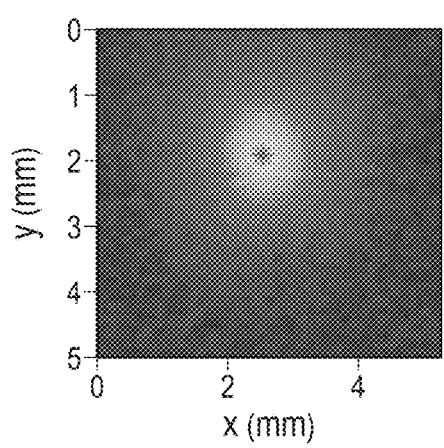
Figure 4D:
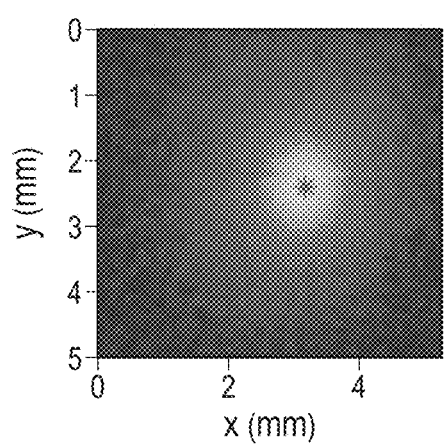
Figures 4E, 4F:
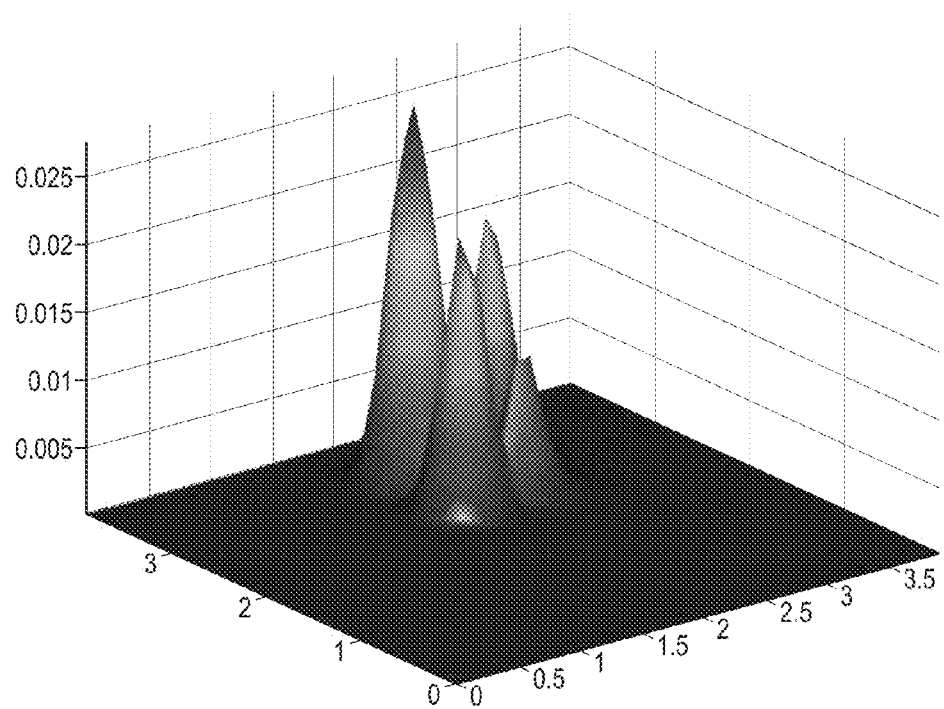
FIG. 4E is an x-y-z image of light reflecting from four reflectors.
FIG. 4F is a JET color map that is employed in FIGS. 4A-4E.

FIG. 4E is an x-y-z image (or equivalently x-y-t image) of light reflecting from four reflectors. In FIG. 4E, the vertical dimension is the z-dimension. Different positions along the vertical axis correspond to different depths of reflectors (or, equivalently, different times-of-arrival of light from the reflectors). FIGS. 4A, 4B, 4C and 4D are x-y planar slices of the x-y-z image in FIG. 4E. These x-y slices were taken at different times-of-arrival at the THz-TDS detector.

In FIGS. 4A, 4B, 4C, 4D, 4E, the light that is recorded is the impulse response of the reflectors to a single pulse of terahertz light emitted by a THz-TDS spectrometer. This single pulse travels from the spectrometer, through the sample, and to the respective reflectors, which reflect it back as separate pulses due to the different depths of the reflectors (a separate pulse for each reflector). These separate reflected pulses then pass through the sample and travel back to the spectrometer.

In some implementations, window functions are used to separate data for each reflector.

FIG. 4F is a JET color map that is employed in FIGS. 4A, 4B, 4C, 4D and 4E. Different colors in this JET color map correspond to different values of normalized intensity. Specifically, the higher (vertically) a color is in the JET color map shown in FIG. 4F, the greater the intensity of incident light.

Figure 5A:
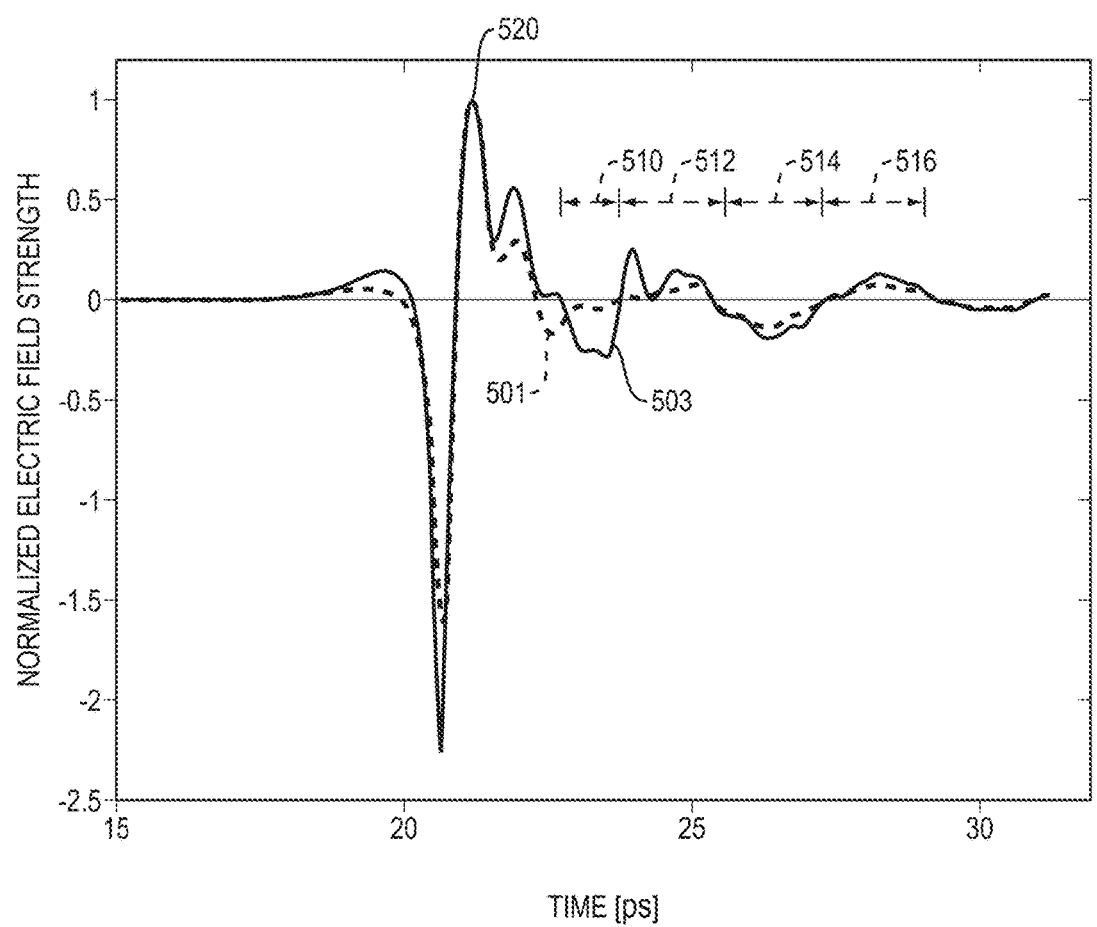
FIGS. 5A and 5B are charts of measurements taken by a single pixel of a THz-TDS detector.
Figure 5B:
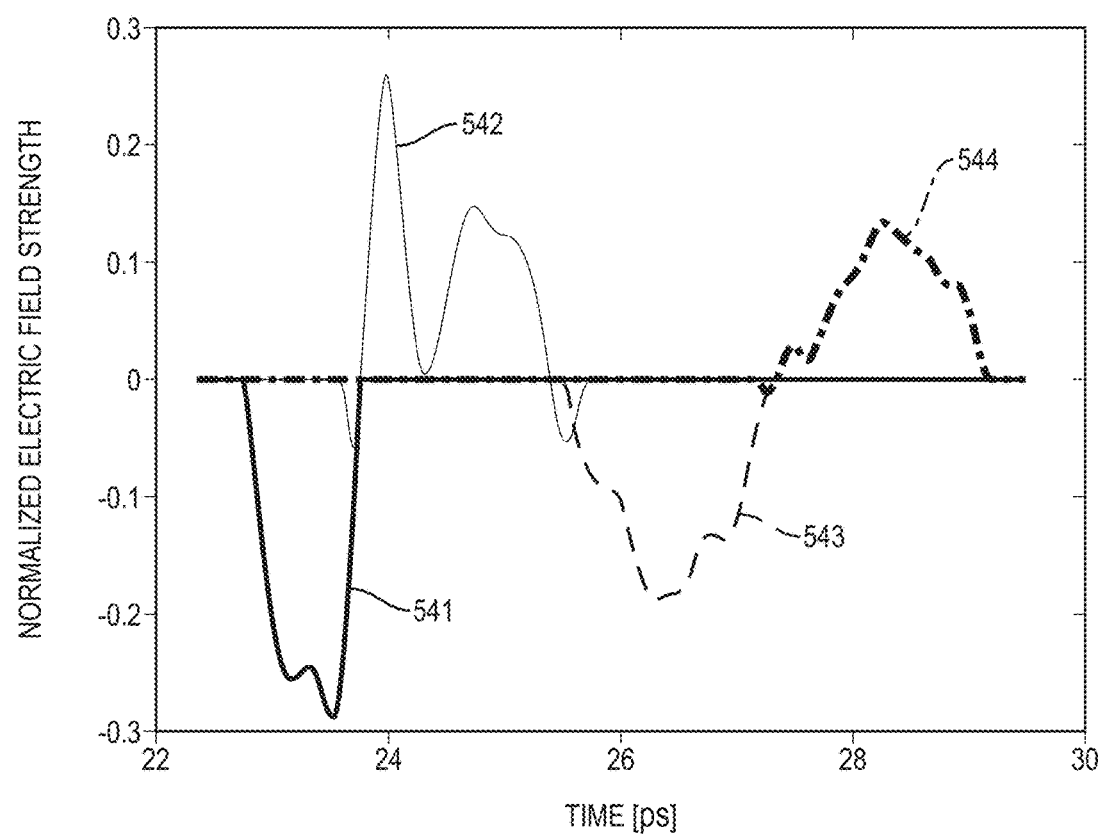

FIGS. 5A and 5B are charts of measurements taken by a single pixel of a THz-TDS spectrometer, in an illustrative implementation of this invention.

FIG. 5A is a chart of normalized electric field strength vs. time, for measurements taken by a single pixel of a THz-TDS detector. (Recall that a THz-TDS detector measures an electric field strength that is proportional to intensity of light).

In FIG. 5A, solid line 503 represents measurements taken when a 2×2 array of four reflectors are beneath the sample. The dominant peak 520 of signal 503 records a pulse of light that reflected directly back from the sample. Four smaller peaks or troughs (specifically, a trough, then a peak, then a trough, then a peak) of signal 503 occur later during time intervals 510, 512, 514, 516, respectively. These smaller peaks or troughs of signal 503 correspond to fainter pulses of light that return from the first, second, third and fourth reflectors, respectively.

In FIG. 5A, dotted line 501 represents measurements taken when no reflectors are beneath the sample. Again, the dominant peak 520 of signal 501 records a pulse of light that reflected directly back from the sample. Small peaks and troughs occur later in signal 501, corresponding to interreflections that occur in the sample itself.

FIG. 5B is a chart of normalized electric field strength vs. time, for measurements taken by a single pixel of a THz-TDS detector. FIG. 5B shows four separate signals 541, 542, 543, 544 caused by reflections from four reflectors, respectively. These four signals are separated in time (except for a short period of overlap at the beginning or end of the signals).

In FIGS. 5A and 5B, the electric field strength is normalized to the positive peak, not the entire range.

FIGS. 6A-6G are images captured by a THz-TDS spectrometer, in an illustrative implementation of this invention.

Figure 6A:
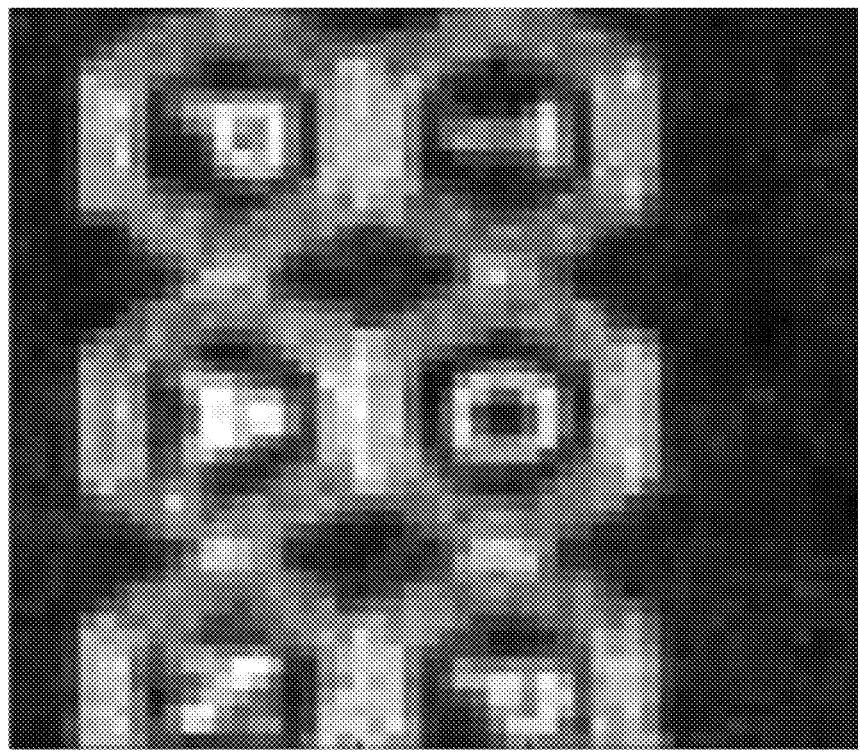
FIG. 6A is an image formed by THz light that reflected directly from a sample, and did not pass through the sample to the reflectors beneath.

FIG. 6A is an image formed by THz light that reflected directly from a sample, and did not pass through the sample to the reflectors beneath. This direct reflection produces the dominant peak of the reflected light signal returning to the detector of the THz-TDS spectrometer (see dominant peak 520 in FIG. 5A). In FIG. 6A, this sample comprises paper with hexagonal metallic patterns that contains the letters "T O P P a N". In FIG. 6A: (a) the SNR (signal-to-noise ratio) of the image is high because the metal in the sample is very reflective in the terahertz range of frequencies; (b) because the SNR is high, the image is clear; and (c) however the resolution (50×50) in FIG. 6A is lower than the resolution in the super-resolved image (100×100) in FIG. 6G, because the data in FIG. 6A is from the dominant peak.

Figure 6B:
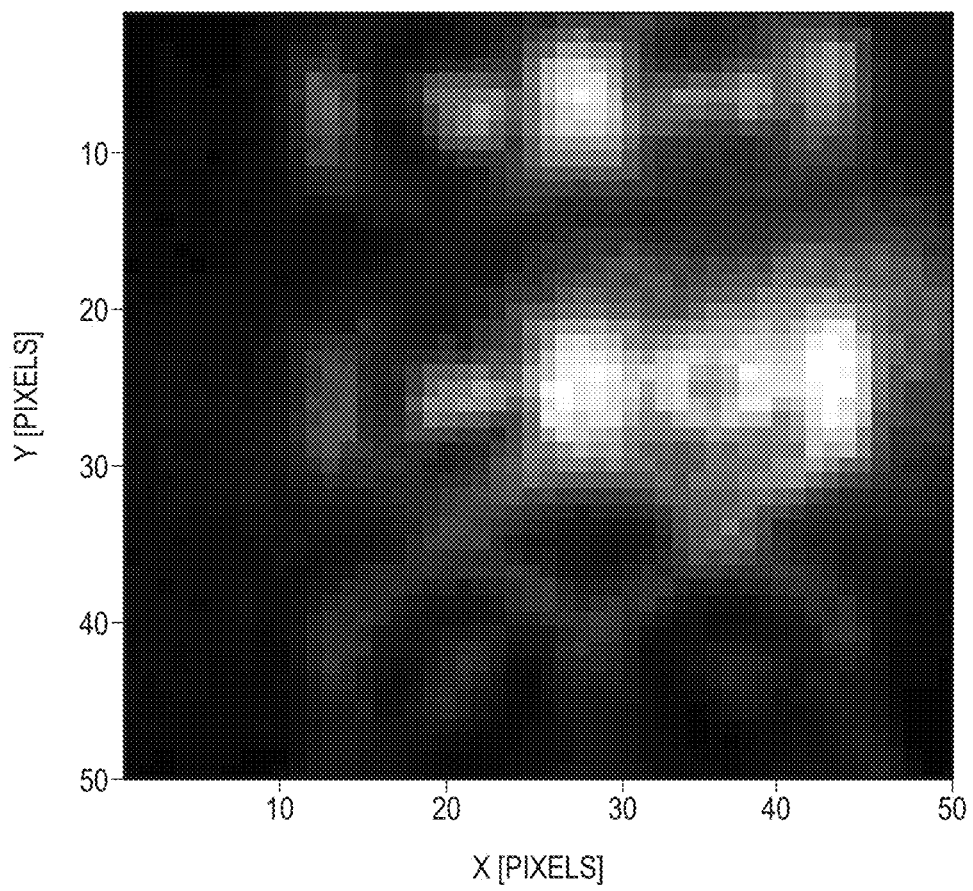
FIG. 6B is an image formed by THz light that reflected internally within the sample.
Figure 6C:
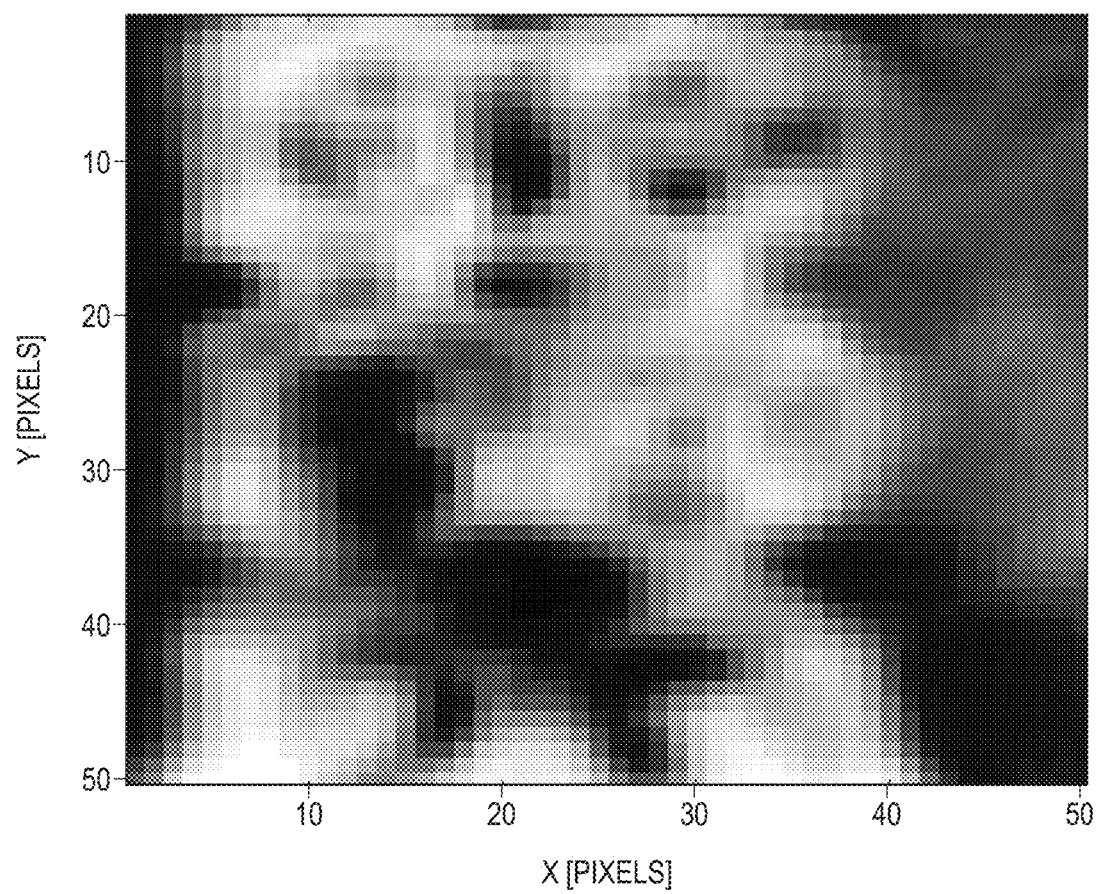
FIGS. 6C-6F are images formed by THz light that was emitted by a THz-TDS spectrometer, then passed through the sample, then reflected from a reflector, and then passed through the sample again.
Figure 6D:
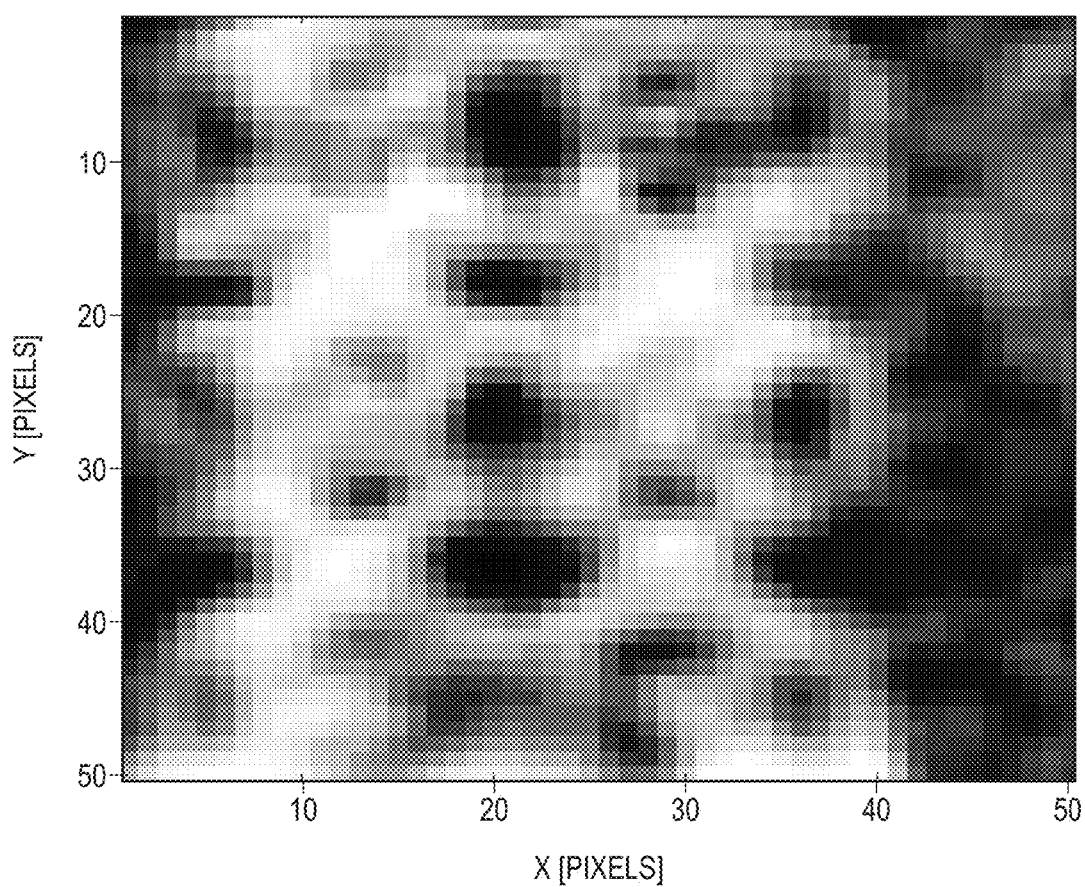
Figure 6E:
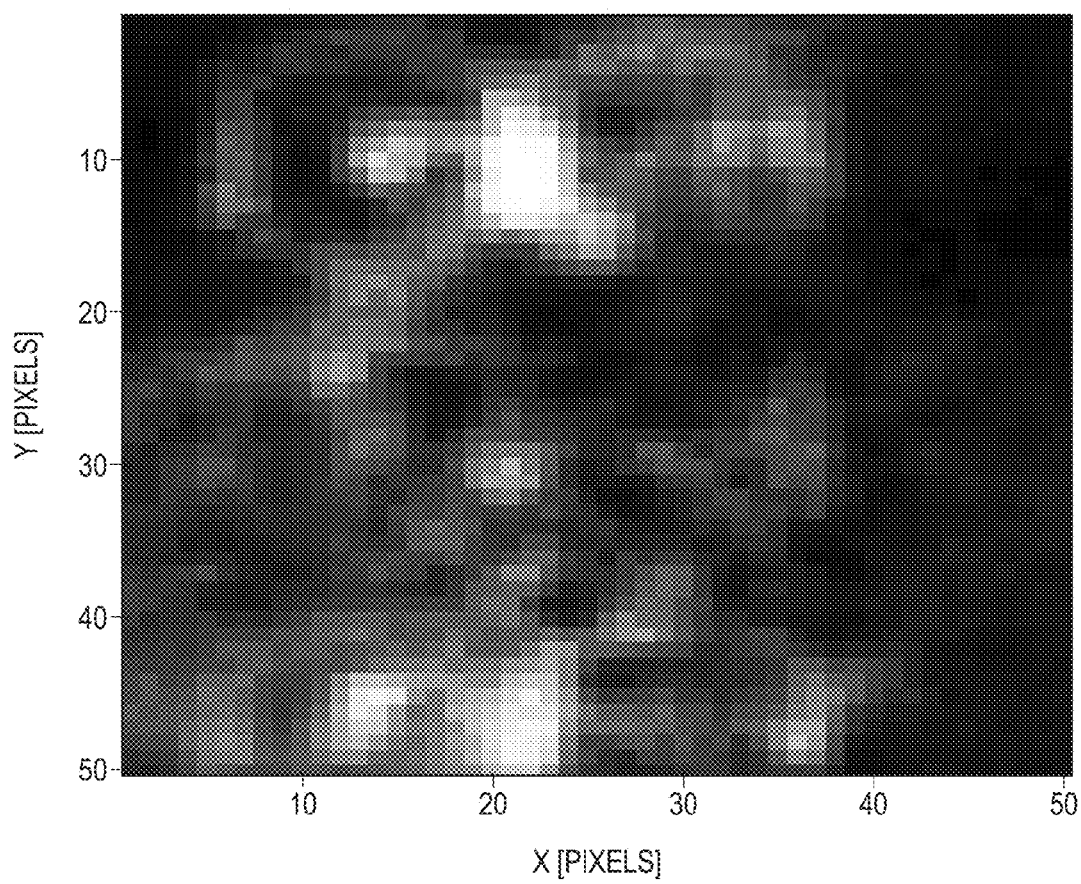
Figure 6F:
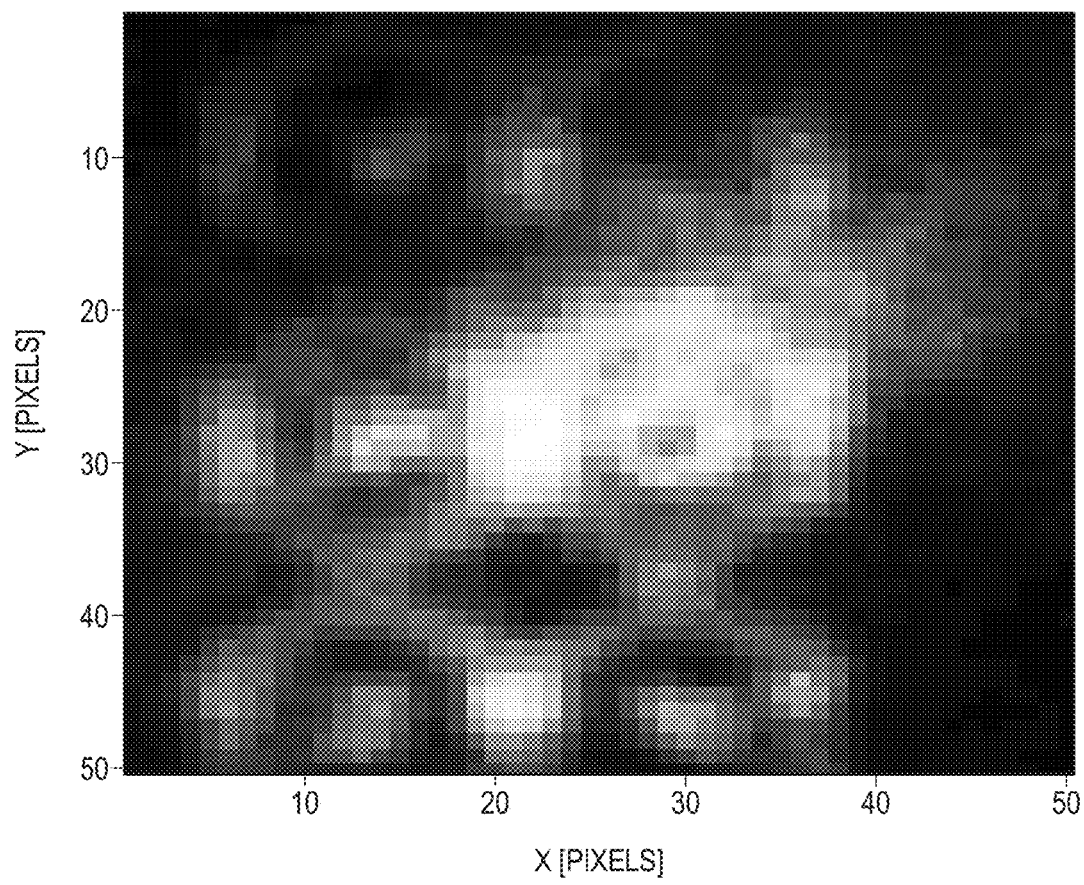

FIG. 6B is an image formed by THz light that reflected internally within the sample, before traveling back to the detector of the THz-TDS detector. This shows that, even though the sample was very thin, some interreflections inside the sample occurred.

FIGS. 6C-6F are images formed by THz light that was emitted by a THz-TDS spectrometer, then passed through the sample, then reflected from a reflector, and then passed through the sample again. In FIGS. 6C, 6D, 6E, 6F, the light that reflected from a first, second, third and fourth reflector, respectively. FIGS. 6C, 6D, 6E, 6F were each captured during a different interval of time, corresponding to when light reached the THz-TDS detector from the first, second, third and fourth reflector, respectively.

Figure 6G:
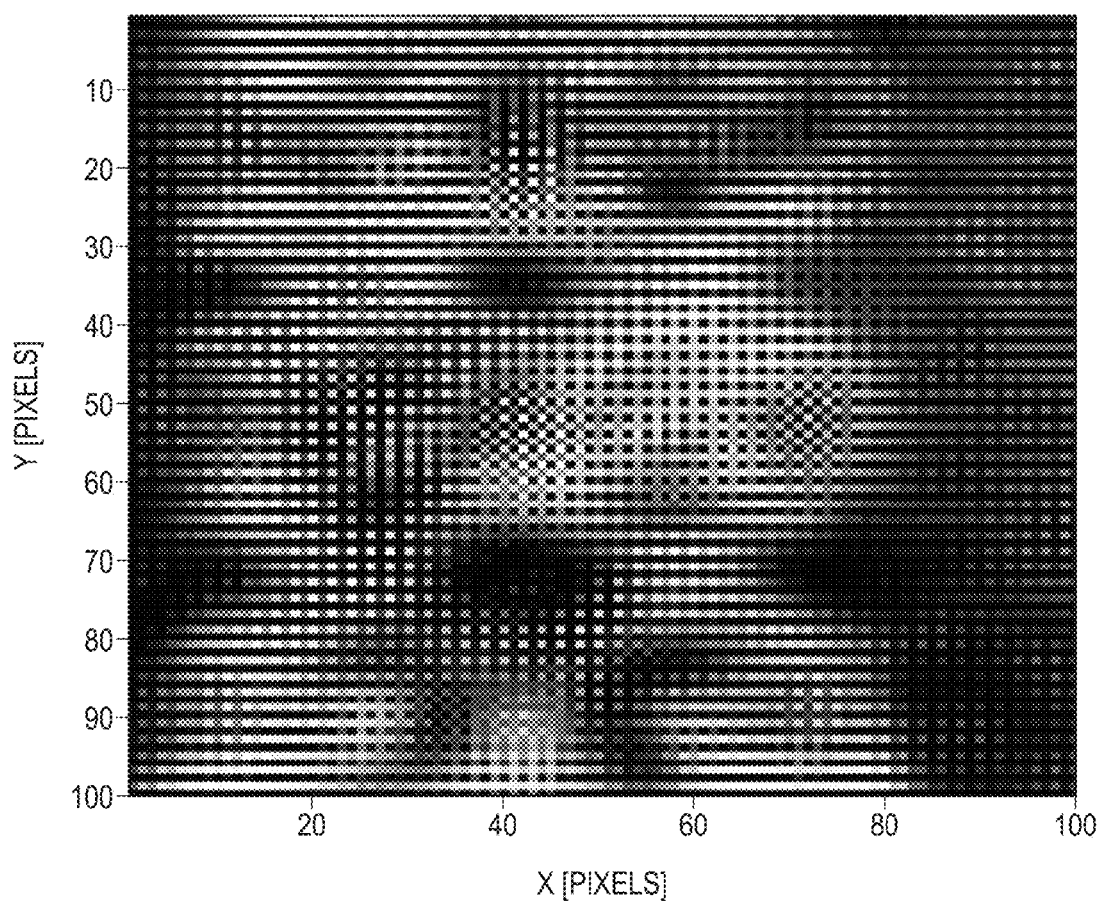
FIG. 6G is a super-resolved image.

FIG. 6G is a super-resolved image, with a 100×100 spatial resolution in the x and y dimensions. Thus, the minimum resolvable x, y distance in FIG. 6G is reduced by a factor of 2 (as compared to the image in FIG. 6A), and the amount of information in FIG. 6G is four times greater than in FIG. 6A. However, in FIGS. 6A-6G, metallic material in the sample makes the sample very reflective in the terahertz range of frequencies. Thus, the SNR of the images in FIGS. 6C-6F (which record or are derived from data regarding fainter reflections from the reflectors) is an order of magnitude lower than the SNR of the image in FIG. 6A (which records the brighter direct reflection from the sample). This low SNR reduces the clarity of the image in FIG. 6G. However, much better clarity in the super-resolved image may be achieved by choosing other materials for the sample.

To generate FIGS. 6A-6F: (a) time-domain signals were measured by a THz-TDS detector; and (b) each of these time-domain signals were multiplied by a window function, then transformed by an FFT (fast Fourier transform), and then integrated over a 1.2 THz to 2.3 THz range of frequencies in the Fourier domain.

In some implementations, the reflectors are staggered in depth beneath the sample, in such a way that pulses of light reflecting back from the reflectors arrive at a THz-TDS detector sensor during a different time interval for each reflector. The detector may temporally resolve—that is, measure separately during different time intervals—the terahertz pulses that arrive at different times from different reflectors. The detector may thus acquire a set of separate measurements, each of which, respectively, measures a terahertz pulse of light that reflected from a particular reflector during a particular time interval. One or more computers may then combine these separate measurements to create a spatially super-resolved image.

In this super-resolved image, there may be a spatially resolved, separately measured light intensity for the tiny x-y region of the sample that is directly above each reflector, respectively—even though the tiny x-y regions that correspond to the reflectors may be so small that the diffraction barrier would ordinarily prevent them from being spatially resolved. This is because the THz-TDS detector may take a separate measurement for each reflector (and its corresponding tiny x-y area of the sample), respectively. This ability to measure light from each reflector (and its corresponding tiny x-y region of the sample) separately may arise because: (a) for each reflector, light that reflects from the reflector passes though a corresponding tiny x-y region of the sample (while traveling to and from the reflector); (b) the reflectors are staggered in depth in such at way that light from each reflector (and its corresponding x-y region of the sample), reaches the THz-TDS detector during a different time interval; and (c) the light sensor takes a separate measurement during each of these different time intervals. Thus, there may be a separate measurement of light that reflects from each reflector (and its corresponding x-y area of the sample), respectively. Then the separate measurements taken at the separate times may be computationally combined to generate a spatially super-resolved image.

As noted above, the separate measurements for each reflector may be acquired by separating data in post-processing.

FIGS. 7, 8, 10 and 11 are flow-charts of imaging methods, in illustrative implementations of this invention.

Figure 7:
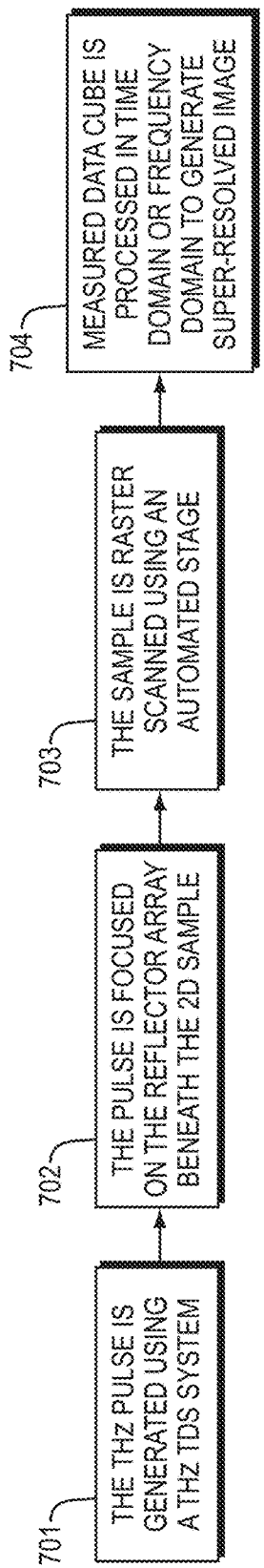
FIG. 7 is a flow-chart of a method for THz-TDS imaging which employs a set of reflectors that are staggered in depth beneath a sample.

FIG. 7 is a flow-chart of a method for THz-TDS imaging which employs a set of reflectors that are staggered in depth beneath a sample. In the example shown in FIG. 7, the method includes the following steps: A terahertz pulse is generated using a THz-TDS system (Step 701). The pulse is focused on the reflector array beneath the 2D sample. In the preceding sentence, to say that a sample is "2D" means that the thickness of the sample is less than ten times the wavelength of light illuminating the sample (Step 702). The sample is raster scanned using an automated stage (Step 703). Measured data cube is processed in time domain or frequency domain to create a super-resolved image (Step 704).

Figure 8:
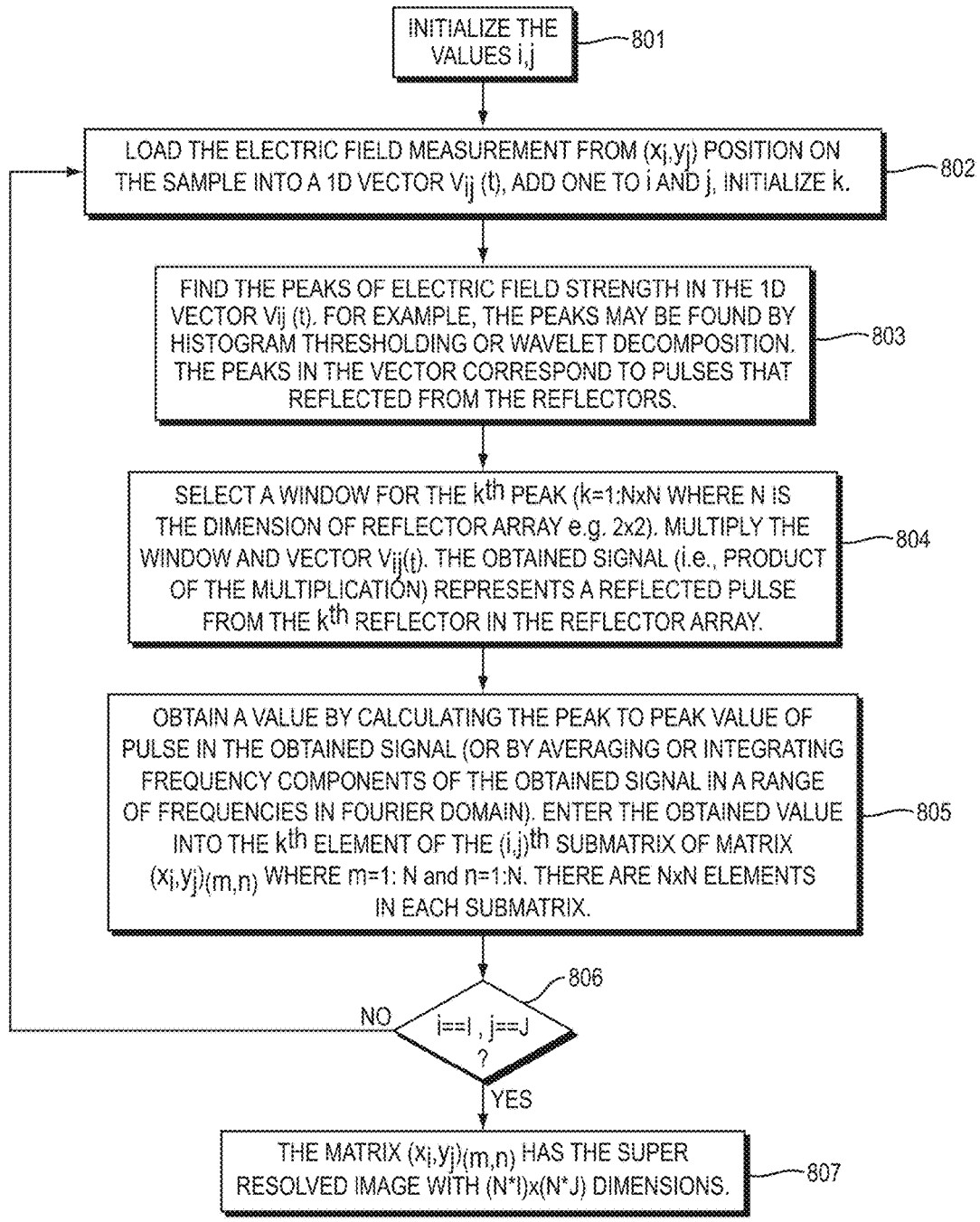
FIG. 8 is a flow-chart of a method for creating a super-resolved image of a sample, by processing THz-TDS measurements of light that has reflected from a set of reflectors that are staggered in depth beneath the sample.

FIG. 8 is a flow-chart of a method for creating a super-resolved image of a sample, by processing THz-TDS measurements of light that has reflected from a set of reflectors that are staggered in depth beneath the sample. In the example shown in FIG. 8, the method includes the following steps: Initialize the values of i and j (Step 801). Load the electric field measurement from the $(x_i, y_j)$ position on the sample into a 1D vector $v_{ij}(t)$, add one one to i and j, and intialize k (Step 802). Find the peaks of electric field strength in the 1D vector $v_{ij}(t)$. For example, the peaks may be found by histogram thresholding or wavelet decomposition. The peaks in this vector correspond to pulses reflected from the reflectors (Step 803). Select a mathematical window function for the $k^{th}$ peak (k=1:N×N where N×N are the dimensions of the reflector array, e.g., 2×2). Element-wise multiply the window function and the 1D vector $v_{ij}(t)$. The obtained signal (i.e., product of the multiplication) represents a reflected pulse from the $k^{th}$ reflector in the reflector array (Step 804). Obtain a value by calculating the peak-to-peak value of a pulse in the obtained signal (or by averaging or integrating frequency components of the obtained signal in a range of frequencies in the frequency domain). Enter the obtained value into the $k^{th}$ element of the $(i,j)^{th}$ submatrix of matrix $(x_i, y_j)_{(m,n)}$, where m=1:N and n=1:N. There are N×N elements in each submatrix (Step 805). Determine whether i is equal to I and whether j is equal to J. If no, go to Step 802, if yes, go to Step 807 (Step 806). The matrix $(x_i, y_j)_{(m,n)}$ has the super-resolved image with dimensions of (N*I)× (N*J) (Step 807).

In Step 804 (FIG. 8) and Step 1104 (FIG. 11), multiplying by a window function has at least two advantages. First, it may separate data into different time bins. Second, if the signal is converted to the frequency domain in later steps (e.g., Steps 805 or 1105), then multiplying by the window first may reduce spectral leakage.

In Steps 804 and 1104, the window may be any type of mathematical window function. For example, the window may a non-negative, smooth, "bell-shaped" curve. In some cases, the window function is zero-valued outside of a selected interval. In some other cases, the window function has tails that go rapidly toward zero. Examples of a window function that may be multiplied in Steps 804 and 1104 include a Gaussian window, confined Gaussian window, generalized normal window, Tukey window, DPSS (discrete prolate spheriodical sequence) window, exponential or Poisson window, Bartlett-Hann window, Planck-Bessel window, Hann-Poisson window, rectangular window, B-spline window, triangular window, Welch window, sine window, cosine-sum window, Hann window, Hamming window, Blackman window, Nuttall window (continuous first derivative), Blackman-Nuttall window, or Blackman-Harris window.

In Steps 804 and 1104, a window function may be selected for the $k^{th}$ peak by choosing a time-domain window function that: (a) is non-zero at the time that the $k^{th}$ peak occurs; or (b) (in the case of a window that has tails that merely approach zero) is not converging rapidly to zero at the time that the $k^{th}$ peak occurs. Or, in some cases, a window function may be chosen, where the window function is bell-shaped and the $k^{th}$ peak of light occurs during the "bell".

In Steps 805 and 1105, an FFT (fast Fourier transform) may be performed and then the frequency components of the spectrum may be averaged or integrated over a range of frequencies. This averaging or integrating in the Fourier domain may mitigate phase mismatch that may otherwise occur between light that reflects from adjoining positions on the sample.

In Steps 805 and 1105, frequency components may be averaged or integrated over a frequency range. This frequency range may be chosen to include a large portion of the spectral energy or spectral power of the spectrum.

The examples shown in FIGS. 7, 8, 10 and 11 are non-limiting. Many other approaches may be employed: (a) to recognize peaks in measured data; (b) to separate measured data into separate bins for different time periods, and (c) to combine separate measurements taken at different times.

OCT Imaging with Staggered Reflectors Beneath Sample

In some implementations of this invention, an OCT (optical coherence tomography) imaging system is employed to capture light that reflects from reflectors beneath the sample.

FIG. 9 shows hardware for an OCT imaging system that includes reflectors staggered at different depths beneath the sample, in an illustrative implementation of this invention. In the example shown in FIG. 9, the OCT imaging system 900 includes a low-coherence light source 907, beamsplitter 905, camera 901, sample arm 910 and reference arm 940. Reference arm 910 includes reference mirror 903 and actuator 902. Actuator 902 comprises one or more motors that actuate rotational movement(s) of reference mirror 903 about one or more axes (to scan the mirror) and actuate translation of mirror 903 to increase or decrease optical path length in the reference arm 903. For example, in some cases, mirror 903 may be translated to adjust for different depths of different reflectors (e.g., to keep the difference between the optical path lengths of the sample arm and reference arm less than the coherence length).

In FIG. 9, sample arm 940 includes lens 924, stage 921, actuator 923, reflectors 941, 942, 943, 944 and elongated structures 911, 912, 913, 914. Each reflector (e.g., 941, 942, 943, 944) comprises a flat upper surface of an elongated structure (e.g., 911, 912, 913, 914). Each elongated structure may, for example, comprise a wire, pin, or nanopillar, and may, in some cases, be covered with resonant structures to increase reflectivity. Stage 921 supports sample 932. Actuator 923 actuates x and y motion of stage 921 and thus sample 932. Actuator 923 may comprise one or more motors. In FIG. 9, lens 924 and reflectors 941, 942, 943, 944 may remain stationary, relative to the imaging system as a whole, while the sample is rastered in the x and y dimensions.

In FIG. 9, a computer 930 may control and interface with microcontrollers 992, 994, 996, 998, which in turn may control and interface with light source 907, camera 901, actuator 923, and actuator 903, respectively. Computer 930 may output instructions that cause the light source, camera and actuators to operate in a synchronized manner. For example, the computer 930 may output instructions that cause the actuated stage to raster the sample to a new x, y position, and then cause the light source to emit a light pulse and the light sensor to capture an image, while the sample is in this new x, y position. Computer 930 may store data in, and access data from, memory device 990. In FIG. 9, devices in the imaging system may communicate with each other via a set of wires (e.g., 981, 982, 983, 984). Alternatively, in some cases, devices in the imaging system may employ wireless modules (e.g., 991, 993, 995, 997) to communicate with each other by wireless communication.

In FIG. 9, sample 932 is translucent, in the frequency range of light that illuminates the sample. For example, in some cases, sample 932 is translucent to, and illuminated by, infrared light. Preferably, sample 932 is thin in the z-dimension (e.g., with a thickness that is less than ten times the wavelength of light illuminating the sample). This tends to reduce interreflections within the sample and to increase transmission of light through the sample.

This invention is not limited to the OCT hardware shown in FIG. 9. In some implementations of this invention, any type of OCT imaging technology (hardware and method) may be employed, including TD-OCT (time domain OCT), FD-OCT (frequency domain OCT), SFED-OCT (spatially encoded frequency domain OCT), TEFD-OCT (time-encoded frequency domain OCT), and FF-OCT (full-field OCT).

In some implementations of this invention, an OCT scan is performed in such a way that the reflectors are always beneath the region of the sample that is then being sampled. Any type of OCT scanning be employed for this purpose. For example, in some implementations, one or more of the following OCT scanning approaches may be employed for this purpose (in addition to or instead of the rastering described above): (i) axial depth scan (also called A-scan), (ii) linear scan to create a cross-sectional tomograph by combining A-scans (also called a B-scan), or (iii) an area scan to create a volumetric image. For example, in some cases, the OCT scanning (i) may be performed by electric motors actuating linear or rotational movement, (ii) may be performed by a CCD (charge-coupled device) camera capturing an en face image of a sample that is full-field illuminated, or (iii) may be performed by a 2D smart detector array.

In some implementations: (a) an OCT system emits a series of pulses of light; (b) for each emitted pulse, the reflectors (which are staggered in depth) reflect back a time-sequence of fainter pulses (which pass through the sample); and (c) pulses of light reflecting back from the reflectors arrive at a light sensor during a different time interval for each reflector. The light sensor may temporally resolve—that is, measure separately during different time intervals—the pulses that arrive at different times from different reflectors.

Alternatively, in some cases: (a) an OCT system emits non-pulsed (e.g., continuous wave) light; (b) the reflectors (which are staggered in depth) reflect back the light, in such a way that the light passes through the sample; and (c) light reflecting back from the reflectors arrives at a light sensor with a different range of phases for each reflector. The different range of phases may arise because the round-trip distance (that light travels to and from a reflector) varies and thus the amount of time elapsed during the round-trip varies, for different reflectors. The light sensor may separately measure the light in different ranges of phases, where each range of phases corresponds to a particular reflector. In this alternative approach, phase is a proxy for time, because the amount of time that elapses during the round-trip may determine the phase of the reflected light that is incident at the light sensor.

In either approach (measuring returning pulses during different time intervals or measuring ranges of phases separately), the OCT light sensor may acquire a set of separate measurements, each of which, respectively, corresponds to a particular reflector. One or more computers may then combine these separate measurements to create a spatially super-resolved image.

In this super-resolved image, there may be a spatially resolved, separately measured light intensity for the tiny x-y region of the sample that is directly above each reflector, respectively—even though the tiny x-y regions that correspond to the reflectors may be so small that the diffraction barrier would ordinarily prevent them from being spatially resolved. This is because the OCT light sensor may take a separate measurement for each reflector (and its corresponding tiny x-y area of the sample), respectively.

Figure 10:
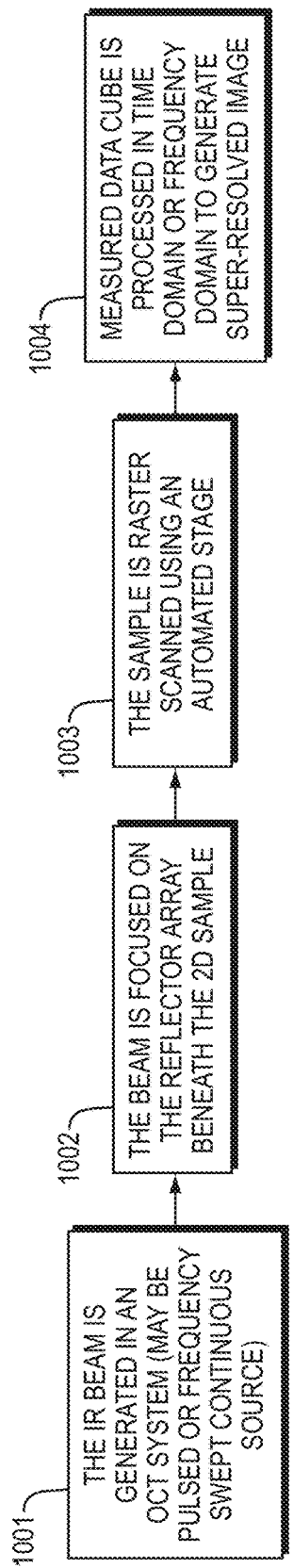
FIG. 10 is a flow-chart of a method for OCT imaging which employs a set of reflectors that are staggered in depth beneath a sample.

FIG. 10 is a flow-chart of a method for OCT imaging which employs a set of reflectors that are staggered in depth beneath a sample. In the example shown in FIG. 7, the method includes the following steps: An infrared beam of light is generated by an OCT system. For example, the IR beam may be pulsed or may be frequency swept continuous source (Step 1001). The beam is focused on the reflector array beneath the 2D sample. In the preceding sentence, to say that the sample is "2D" means that the thickness of the sample is less than ten times the wavelength of light illuminating the sample (Step 1002). The sample is raster scanned using an automated stage (Step 1003). Measured data cube is processed in time domain or frequency domain to create a super-resolved image (Step 1004).

Figure 11:
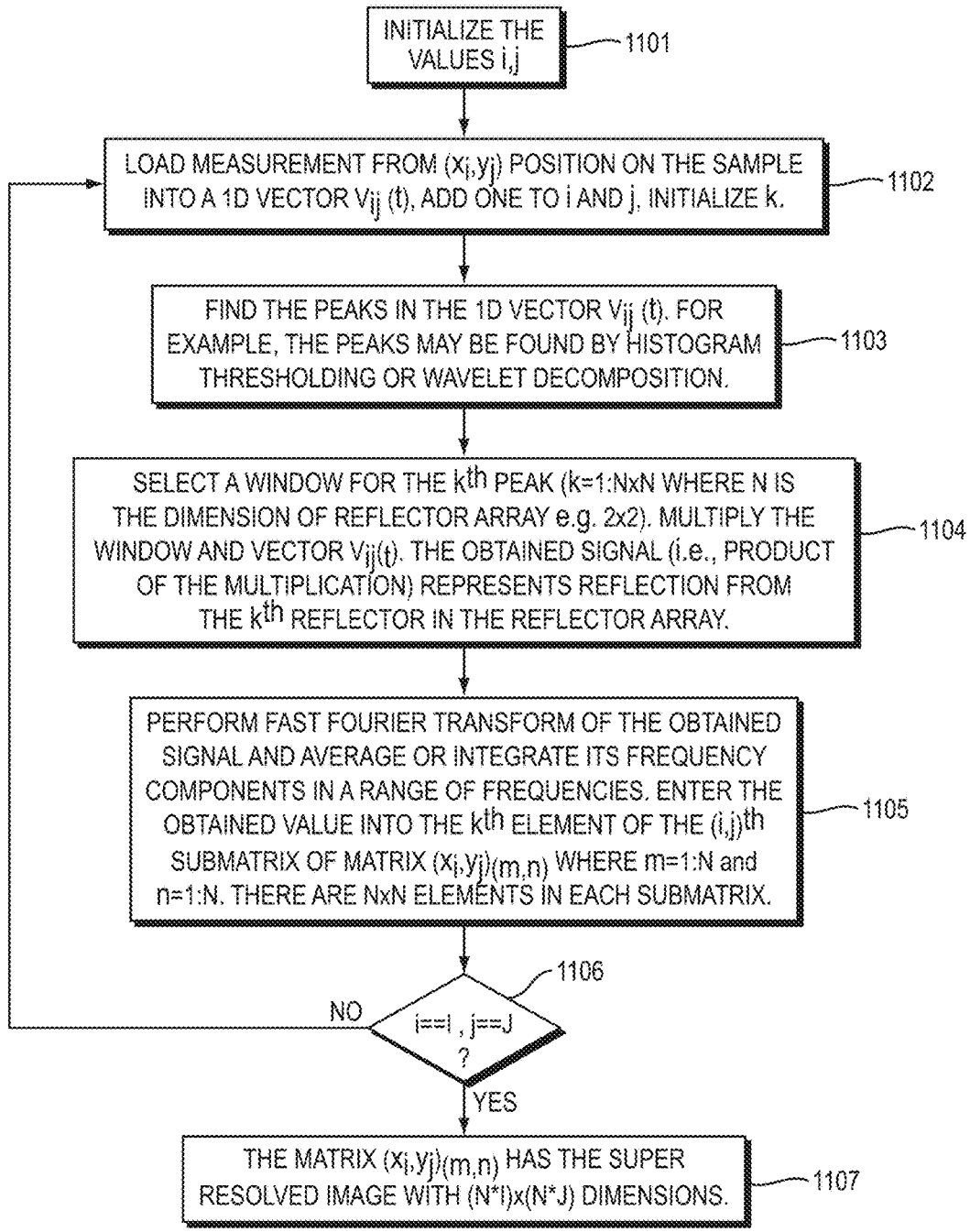
FIG. 11 is a flow-chart of a method for creating a super-resolved image of a sample, by processing OCT measurements of light that has reflected from a set of reflectors that are staggered in depth beneath the sample.

FIG. 11 is a flow-chart of a method for creating a super-resolved image of a sample, by processing OCT measurements of light that has reflected from a set of reflectors that are staggered in depth beneath the sample. In the example shown in FIG. 8, the method includes the following steps: Initialize the values of i and j (Step 1101). Load the measurement from the $(x_i, y_j)$ position on the sample into a 1D vector $v_{ij}(t)$, add one one to i and j, and intialize k (Step 1102). Find the peaks in the 1D vector $v_{ij}(t)$. For example, the peaks may be found by histogram thresholding or wavelet decomposition (Step 1103). Select a mathematical window function for the $k^{th}$ peak (k=1:N×N where N×N are the dimensions of the reflector array, e.g., 2×2). Element-wise multiply the window and the 1D vector $v_{ij}(t)$. The obtained signal (i.e., product of the multiplication) represents reflection from the $k^{th}$ reflector in the reflector array (Step 1104). Perform Fast Fourier Transform of the obtained signal and average or integrate its frequency components in a range of frequencies in the frequency domain. Enter the obtained value into the $k^{th}$ element of the $(i,j)^{th}$ submatrix of matrix $(x_i, y_j)_{(m,n)}$, where m=1:N and n=1:N. There are N×N elements in each submatrix (Step 1105). Determine whether i is equal to 1 and whether j is equal to J. If no, go to Step 1102, if yes, go to Step 1107 (Step 1106).

The matrix $(x_i, y_j)_{(m,n)}$ has the super-resolved image with dimensions of (N*I)×(N*J) (Step 1107).

As noted above, this invention is not limited to the algorithms shown in FIGS. 7, 8, 10 and 11. For example, many different algorithms may be employed to find peaks and to separate them, including wavelet decomposition, canny edge detection, and CLEAN deconvolution.

Model

The discussion in this "Model" section describes how (loosely speaking) spatial information may be encoded in time, in an illustrative THz-TDS embodiment of this invention.

Let the vector X=(x y, z). For transmission-mode THz-TDS the measured returning field for a simple reflection point through a 3D sample may be given as:

$$E^-(X,f) = \rho(X,f) E^+(X,f) \quad\quad \text{Eq. 1}$$

where $E^+(X,f)$ is the emitted THz pulse spectrum, $E^-(X,f)$ is the Fourier transform of the measured field, and $\rho(X,f)$ is the reflection spectrum of the sample which is influenced by complex permittivity and absorption spectrum of the sample.

THz-TDS may measure the temporal profile of a complex field reflected from the sample. Therefore, it is convenient to start from the Fourier domain and assume that THz-TDS is a broadband confocal imaging system with no pupil function which measures both the phase and amplitude of the Fourier signal. Based on confocal image formation framework the complex image at Fourier domain may be expressed as:

$$E^-(X,t) = F^{-1}\{[\rho(X,f) E^+(X,f)] *_X h(X,f)\} \quad\quad \text{Eq. 2}$$

where $h(X,f)$ is the wavelength dependent point spread function (PSF) of the THz system and $*_X$ is the convolution operator in X space.

The low power level at THz-TDS (often less than 1 μWatt) may not allow a pupil at the detection side to shape the PSF and therefore there may be no pupil function involved. Eq. 2 is the general confocal image formation expression for TDS system with a 3D sample. In an illustrative implementation of this invention, we may break down the 3D sample to a 2D sample at z0 and a sparse set of N 2D subwavelength reflectors Ri (x, y) beneath it at z1, z2, . . . zN to encode subwavelength 2D spatial resolution into each temporal measurement as in Equation 3.

$$E^-(X,t) \cong F^{-1}\{[(\rho(x,y,f) e^{-j\omega z_0} + (1-\rho(x,y,f))^2 \Sigma_{i=1}^N R_i(x,y) e^{-j\omega z_i}) E^+(X,f)] *_X h(X,f)\} \quad\quad \text{Eq. 3}$$

To better understand how Equation 3 works, let's assume that the incident field has a planar uniform wavefront at the foci ($E^i(X,f) = E_{THz}^-(f)$), the PSF and sample profile are independent of wavelength ($h(X,f) = h(X)$, $\rho(x,y,f) = \rho(x,y)$, and the focus point is not scanned in z ($E^-(X,t)_{z=cte} = E^-(x, y, t)$). In this case for a single rectangular reflector (R1(x,y)=r1rect(2x,2y)) Equation. 3 may be reduced to:

$$E^-(x, y, t) \cong F^{-1} \quad\quad \text{Eq. 4}$$

$$\{[(\rho(x, y) e^{-j\omega z_0} + (1 - \rho(x, y))^2 r_1 rect(2x, 2y) e^{-j\omega z_1}) E^+(f)] *_X$$

$$h(X)\} = [\rho(x, y) *_X h(x, y, z_0)] \delta\left(t - \frac{2nz_0}{c}\right) *_t$$

$$E_{THz}(t) + [(1 - \rho(x, y))^2 r_1 rect(2x, 2y) *_X h(x, y, z_1)]$$

$$\delta\left(t - \frac{2nz_1}{c}\right) *_t E_{THz}(t)$$

In Equation 4, r1 is the reflection coefficient of the reflector and since the reflection profile of the sample is multiplied by the reflector the intensity information for the reflector may be indirectly encoded to the measured signal. In this equation, the h(x,y,z1) is also convolved with this information. FDTD (finite difference time domain) simulations may be employed to estimate the PSF in 3D.

Unless the context clearly indicates otherwise, the meanings that are assigned to variables in this "Model" section apply only in this "Model" section.

This invention is not limited by this "Model" section. The equations (and mathematical and other descriptions) in this "Model" section merely provide non-limiting examples. This invention may be implemented in many other ways.

Software

In the Computer Program Listing above, five computer program files are listed. These five computer program files comprise software employed in a prototype implementation of this invention. To run these as Matlab® software files, the filename extension for each would be changed from ".txt" to ".m". Here is a description of these five computer program files:

(1) Thz_Subwavelength.txt: This file encodes a software program that reads the THz-TDS measurements and creates an output higher resolution image. The Thz_Subwavelength program does this by finding the peaks and then multiplying by a window "bell-shaped" function to tune into each peak. The window functions are multiplied by the raw data, so that data from only specific sections are used. The raw signals are plotted to find location of peaks. The super-resolved image is shown in frequency domain. The highest frequency components of each peak are averaged to create a better image This Thz_Subwavelength program calls upon extend, gift's, getThzSuperRes_InterweaveMC.m, Interweaver, which are located in same folder. This Thz_Subwavelength program expects that data is located in the same folder as the software code. The current code parameters may be set initially for most recent data.

(2) extend.txt: This file encodes a function that converts a Matrix A into a given size based on input parameters.

(3) getFFT.txt: This file encodes a function that outputs the fast Fourier transform of a data cube.

(4) getThzSuperRes_InterweaveMC.txt: This file encodes a function that takes four images as input, and interweaves them together to get superresolution.

(5) InterweaveR.txt: This file encodes a function that interweaves rows of matrix together.

This invention is not limited to the software set forth in these five computer program files. Other software may be employed. Depending on the particular implementation, the software used in this invention may vary.

Computers

In illustrative implementations of this invention, one or more computers (e.g., servers, network hosts, client computers, integrated circuits, microcontrollers, controllers, field-programmable-gate arrays, personal computers, digital computers, driver circuits, or analog computers) are programmed or specially adapted to perform one or more of the following tasks: (1) to control the operation of, or interface with, hardware components of an imaging system, including any light source, light sensor, camera, detector, or actuator; (2) to cause the imaging system to acquire separate measurements of light from different reflectors during different time periods; (3) to cause the imaging system to acquire separate measurements of light from different reflectors in different ranges of phases; (4) to find peaks in data; (5) to separate data into different time periods (e.g., by multiplying by a window function) or into different ranges of phases; (6) to perform a fast Fourier transform; (7) to average or integrate frequency components in the Fourier domain; (8) to enter values into a submatrix or matrix; (9) to compute a spatially super-resolved image (e.g., by combining separate measurements taken at different times or by combining separate measurements taken in different ranges of phases); (10) to receive data from, control, or interface with one or more sensors; (11) to perform any other calculation, computation, program, algorithm, or computer function described or implied herein; (12) to receive signals indicative of human input; (13) to output signals for controlling transducers for outputting information in human perceivable format; (14) to process data, to perform computations, to execute any algorithm or software, and (15) to control the read or write of data to and from memory devices (items 1-15 of this sentence referred to herein as the "Computer Tasks"). The one or more computers (e.g. 230, 292, 294, 296, 930, 992, 994, 996) may, in some cases, communicate with each other or with other devices: (a) wirelessly, (b) by wired connection, (c) by fiber-optic link, or (d) by a combination of wired, wireless or fiber optic links.

In exemplary implementations, one or more computers are programmed to perform any and all calculations, computations, programs, algorithms, computer functions and computer tasks described or implied herein. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium may comprise a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers execute programs according to instructions encoded in one or more tangible, non-transitory, computer-readable media. For example, in some cases, these instructions comprise instructions for a computer to perform any calculation, computation, program, algorithm, or computer function described or implied herein. For example, in some cases, instructions encoded in a tangible, non-transitory, computer-accessible medium comprise instructions for a computer to perform the Computer Tasks.

Network Communication

In illustrative implementations of this invention, electronic devices (e.g., 204, 206, 223, 230, 292, 294, 296, 901, 907, 923, 930, 992, 994, 996) are configured for wireless or wired communication with other devices in a network.

For example, in some cases, one or more of these electronic devices each include a wireless module for wireless communication with other devices in a network. Each wireless module (e.g., 291, 293, 295, 991, 993, 995, 997) may include (a) one or more antennas, (b) one or more wireless transceivers, transmitters or receivers, and (c) signal processing circuitry. Each wireless module may receive and transmit data in accordance with one or more wireless standards.

In some cases, one or more of the following hardware components are used for network communication: a computer bus, a computer port, network connection, network interface device, host adapter, wireless module, wireless card, signal processor, modem, router, cables or wiring.

In some cases, one or more computers (e.g., 230, 292, 294, 296, 930, 992, 994, 996) are programmed for communication over a network. For example, in some cases, one or more computers are programmed for network communication: (a) in accordance with the Internet Protocol Suite, or (b) in accordance with any other industry standard for communication, including any USB standard, ethernet standard (e.g., IEEE 802.3), token ring standard (e.g., IEEE 802.5), wireless standard (including IEEE 802.11 (wi-fi), IEEE 802.15 (bluetooth/zigbee), IEEE 802.16, IEEE 802.20 and including any mobile phone standard, including GSM (global system for mobile communications), UMTS (universal mobile telecommunication system), CDMA (code division multiple access, including IS-95, IS-2000, and WCDMA), or LTS (long term evolution)), or other IEEE communication standard.

Actuators

In illustrative implementations, the imaging system includes actuator (e.g., 223, 902, 923). Each actuator (including each actuator for actuating any movement) may be any kind of actuator, including a linear, rotary, electrical, piezoelectric, electro-active polymer, mechanical or electromechanical actuator. In some cases, the actuator includes and is powered by an electrical motor, including any stepper motor or servomotor. In some cases, the actuator includes a gear assembly, drive train, pivot, joint, rod, arm, or other component for transmitting motion. In some cases, one or more sensors are used to detect position, displacement or other data for feedback to one of more of the actuators.

Definitions

The terms "a" and "an", when modifying a noun, do not imply that only one of the noun exists. For example, a statement that "an apple is hanging from a branch": (i) does not imply that only one apple is hanging from the branch; (ii) is true if one apple is hanging from the branch; and (iii) is true if multiple apples are hanging from the branch.

In the context of an imaging system, to say that A is "above" B means that A is optically closer to a light source than B is, the light source being an active light source of the system that illuminates a sample that is imaged by the system. The terms "top", "upper" and similar terms that connote a first thing being above a second thing shall be construed in like manner. For example: (a) in FIG. 2A, sample 232 is "above" reflectors 241, 242, 243, 244; and (b) in FIG. 1C, sample 232 is "above" reflectors 101, 102, 103, 104. To say that A is "above" B does not create any implication regarding the horizontal position of A relative to B. For example: (a) in FIG. 2A, reflector 243 is "above" reflector 242 (despite the difference in their horizontal positions) and reflector 241 is "above" reflector 244 (despite their difference in horizontal positions).

As used herein, an "active light source" means a light source that is configured to emit light. The emission of light by an active light source may be triggered by a laser pulse or by other illumination. Non-limiting examples of active light sources are: (a) lasers, (b) LEDs (light-emitting diodes), (c) crystals that emit light during electro-optic rectification, and (d) photoconductive emitters. Also, here are two negative examples: A mirror that only reflects light (and is not configured to emit light) is not an "active light source". A lens that only transmits light (and is not configured to emit light) is not an "active light source".

In the context of an imaging system that captures an image of a sample, "axial direction" means a direction, relative to the system as whole, that (i) points optically away from an active light source that illuminates the sample and (ii) is parallel to the optical axis of the system. For purposes of the preceding sentence, if the optical axis is folded, then the optical axis shall be treated as being in the local direction of the optical axis at a point immediately above the sample. For example: (a) in FIG. 2A, light is traveling in an "axial direction" when it travels from lens 234 to sample 232 along optical axis 264; and (b) in FIG. 1C, light is traveling in an "axial direction" when it is traveling from the right side to the left side of FIG. 1C along optical axis 131.

To compute "based on" specified data means to perform a computation that takes the specified data as an input.

In the context of an imaging system, to say that A is "below" or "beneath" B means that A is optically farther away from a light source than B is, the light source being an active light source of the system that illuminates a sample that is imaged by the system. The terms "bottom", "lower" and similar terms that connote a first thing being below a second thing shall be construed in like manner. For example: (a) in FIG. 2A, reflectors 241, 242, 243, 244 are "beneath" sample 232; and (b) in FIG. 1C, reflectors 101, 102, 103, 104 are "beneath" sample 232. To say that A is "below" or "beneath" B does not create any implication regarding the horizontal position of A relative to B. For example: (a) in FIG. 2A, reflector 242 is "below" reflector 243 (despite the difference in their horizontal positions) and reflector 244 is "below" reflector 241 (despite their difference in horizontal positions).

The term "comprise" (and grammatical variations thereof) shall be construed as if followed by "without limitation". If A comprises B, then A includes B and may include other things.

The term "computer" includes any computational device that performs logical and arithmetic operations. For example, in some cases, a "computer" comprises an electronic computational device, such as an integrated circuit, a microprocessor, a mobile computing device, a laptop computer, a tablet computer, a personal computer, or a mainframe computer. In some cases, a "computer" comprises: (a) a central processing unit, (b) an ALU (arithmetic logic unit), (c) a memory unit, and (d) a control unit that controls actions of other components of the computer so that encoded steps of a program are executed in a sequence. In some cases, a "computer" also includes peripheral units including an auxiliary memory storage device (e.g., a disk drive or flash memory), or includes signal processing circuitry. However, a human is not a "computer", as that term is used herein.

"Convex hull" is defined above.

"Defined Term" means a term or phrase that is set forth in quotation marks in this Definitions section.

To say that a region of the sample is "directly above" a reflector means that: (a) the region is above the reflector, and (b) a set of points in the region have the same x, y coordinates as a set of points in the reflector.

For an event to occur "during" a time period, it is not necessary that the event occur throughout the entire time period. For example, an event that occurs during only a portion of a given time period occurs "during" the given time period.

The term "e.g." means for example.

Each equation above is referred to herein by the equation number set forth to the right of the equation. For example: "Equation 1" means Equation 1 above; and. "Equation 4" means Equation 4 above. Non-limiting examples of an "equation", as that term is used herein, include: (a) an equation that states an equality; (b) an inequation that states an inequality (e.g., that a first item is greater than or less than a second item); (c) a mathematical statement of proportionality or inverse proportionality; and (d) a system of equations.

The fact that an "example" or multiple examples of something are given does not imply that they are the only instances of that thing. An example (or a group of examples) is merely a non-exhaustive and non-limiting illustration.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each may be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes a "third" thing, a "fourth" thing and so on shall be construed in like manner.

To say that a plane is "horizontal" means that it is parallel to the x-y plane.

"For instance" means for example.

As used herein, a "top view" of an object means a principal orthographic view that shows a normal view of a top side of the object, in such a way that a straight line that is parallel to the z-axis appears as a single point in the normal view.

To say a "given" X is simply a way of identifying the X, such that the X may be referred to later with specificity. To say a "given" X does not create any implication regarding X. For example, to say a "given" X does not create any implication that X is a gift, assumption, or known fact.

"Herein" means in this document, including text, specification, claims, abstract, and drawings.

As used herein: (1) "implementation" means an implementation of this invention; (2) "embodiment" means an embodiment of this invention; (3) "case" means an implementation of this invention; and (4) "use scenario" means a use scenario of this invention.

The term "include" (and grammatical variations thereof) shall be construed as if followed by "without limitation".

To "integrate" means: (a) to perform integration in the calculus sense, or (b) to compute a sum of discrete samples.

"Intensity" means any measure of intensity, energy or power. For example, the "intensity" of light includes any of the following measures: irradiance, spectral irradiance, radiant energy, radiant flux, spectral power, radiant intensity, spectral intensity, radiance, spectral radiance, radiant exitance, radiant emittance, spectral radiant exitance, spectral radiant emittance, radiosity, radiant exposure, radiant energy density, luminance or luminous intensity.

"Light" means electromagnetic radiation of any frequency. For example, "light" includes, among other things, visible light and infrared light. Likewise, any term that relates to light (e.g., "imaging") shall be construed broadly as applying to electromagnetic radiation of any frequency.

Here are some non-limiting examples of a "light sensor": (a) a digital camera; (b) a digital grayscale camera; (c) a digital color camera; (d) a video camera; (e) a light sensor or image sensor, (f) a set or array of light sensors or image sensors; (g) an imaging system; (h) a light field camera or plenoptic camera; (i) a time-of-flight camera; (j) a depth camera; and (k) a detector of a terahertz time-domain spectrometer. A light sensor includes any computers or circuits that process data captured by the light sensor.

As used herein, (i) a single scalar is not a "matrix", and (ii) one or more entries, all of which are zero (i.e., a so-called null matrix), is not a "matrix".

"Maximum dimension" is defined above.

To "multiply" includes to multiply by an inverse. Thus, to "multiply" includes to divide.

To say that an A is moving "optically away" from X means that A is moving in such a way that the optical distance between the A and X is increasing.

To say that B is "optically closer" to X than C is, means that the optical distance between B and X is less than the optical distance between C and X.

To say that B is "optically farther" from X than C is, means that the optical distance between B and X is more than the optical distance between C and X.

To say that A is moving "optically toward" X means that A is moving in such a way that the optical distance between A and X is decreasing.

The term "or" is inclusive, not exclusive. For example, A or B is true if A is true, or B is true, or both A or B are true. Also, for example, a calculation of A or B means a calculation of A, or a calculation of B, or a calculation of A and B.

A parenthesis is simply to make text easier to read, by indicating a grouping of words. A parenthesis does not mean that the parenthetical material is optional or may be ignored.

A path may be a "round-trip", even though it does not start and end at the exact same location. For example, light travels in a "round-trip" when it travels in a path that starts at an active light source of an imaging system, goes to a reflector, and ends at a light sensor of the system.

A non-limiting example of a sensor measuring a first phenomenon "separately" from a second phenomenon is the sensor taking a first set of measurements that is separable (e.g., in post-processing) from a second set of measurements, the first set of measurements being measurements regarding the first phenomenon and not the second phenomenon, and the second set of measurements being measurements regarding the second phenomenon and not the first phenomenon. Another non-limiting example of a sensor measuring a first phenomenon "separately" from a second phenomenon is the sensor taking a first set of measurements and a second set of measurements, in such a way that: (a) the first and second sets of measurements are kept distinct from each other at all times while they are being measured (to the extent that they have then been measured); (b) the first set of measurements are measurements regarding the first phenomenon and not the second phenomenon; and (c) the second set of measurements are measurements regarding the second phenomenon and not the first phenomenon.

As used herein, the term "set" does not include a group with no elements.

As used herein, a "side view" of an object means a principal orthographic view that shows a normal view of a side of the object, in such a way that a straight line that is parallel to the x-axis appears as a single point in the normal view.

Unless the context clearly indicates otherwise, "some" means one or more.

As used herein, a "subset" of a set consists of less than all of the elements of the set.

The term "such as" means for example.

"Terahertz range of frequencies" means 0.3 terahertz to 300 terahertz.

"Terahertz light" or "terahertz radiation" means light in the terahertz range of frequencies.

"Terahertz light source" means an active light source that emits terahertz light.

"Terahertz imaging" means a method of imaging that involves illuminating a sample with terahertz light.

"Terahertz imaging system" means an imaging system that includes a terahertz light source.

"THz" means terahertz.

To say that light travels from A "to" B means that light travels from A directly or indirectly to B. A non-limiting example of light traveling from C "to" D is light traveling in a folded path from C to D, in such a way that the light interacts with other optical elements, such as a lens or mirror, along the folded path between C and D.

To say that a machine-readable medium is "transitory" means that the medium is a transitory signal, such as an electromagnetic wave.

As used herein: (a) the "x-axis", "y-axis", "z-axis" are Euclidean coordinate axes, each of which is perpendicular to the other two; (b) the "z-axis" is parallel to the axial direction; (c) the "x-dimension", "y-dimension" and "z-dimension" are dimensions in a 3D Euclidean space and correspond to the "x-axis", "y-axis", and "z-axis, respectively; (d) "z-distance" means distance in the z-dimension; and (e) "depth" is a measure of position in the z-dimension (i.e., a z-axis coordinate).

"Abbe X-Y Resolution" is defined above.

A matrix may be indicated by a bold capital letter (e.g., D). A vector may be indicated by a bold lower case letter (e.g., a). However, the absence of these indicators does not indicate that something is not a matrix or not a vector.

Except to the extent that the context clearly requires otherwise, if steps in a method are described herein, then the method includes variations in which: (1) steps in the method occur in any order or sequence, including any order or sequence different than that described; (2) any step or steps in the method occurs more than once; (3) any two steps occur the same number of times or a different number of times during the method; (4) any combination of steps in the method is done in parallel or serially; (5) any step in the method is performed iteratively; (6) a given step in the method is applied to the same thing each time that the given step occurs or is applied to different things each time that the given step occurs; (7) one or more steps occur simultaneously, or (8) the method includes other steps, in addition to the steps described herein.

Headings are included herein merely to facilitate a reader's navigation of this document. A heading for a section does not affect the meaning or scope of that section.

This Definitions section shall, in all cases, control over and override any other definition of the Defined Terms. The Applicant or Applicants are acting as his, her, its or their own lexicographer with respect to the Defined Terms. For example, the definitions of Defined Terms set forth in this Definitions section override common usage or any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. To the extent that any term or phrase is defined or clarified herein, such definition or clarification applies to any grammatical variation of such term or phrase, taking into account the difference in grammatical form. For example, the grammatical variations include noun, verb, participle, adjective, and possessive forms, and different declensions, and different tenses.

Variations

This invention may be implemented in many different ways. Here are some non-limiting examples:

In some implementations, this invention is a method comprising illuminating a sample in such a way that light passes through the sample, reflects from a set of reflectors, passes through the sample again and travels to a light sensor, wherein: (a) the reflectors in the set are located beneath the sample and are staggered in depth, each reflector being at a different depth than the other reflectors in the set; and (b) light reflecting from each reflector, respectively, in the set (i) arrives at the light sensor during a time interval that is different than each time interval during which light reflecting another reflector in the set arrives at the light sensor, and (ii) is measured by the light sensor separately from light reflecting from each other reflector, respectively, in the set. In some cases, the light that passes through the sample is pulsed. In some cases: (a) a light source emits pulses of light that pass through the sample and reach the reflectors; and (b) for each of the pulses, respectively, a set of multiple reflected pulses reflects from the set of reflectors, in such a way that each reflected pulse arrives at the light sensor during a time interval that is different than that during which any other reflected pulse arrives at the light sensor. In some cases, the light sensor separately measures each reflected pulse, respectively, in the set of reflected pulses. In some cases, each reflected pulse, respectively, in the set of reflected pulses, is reflected by only one reflector in the set of reflectors. In some cases: (a) the light sensor comprises a detector of a terahertz time-domain spectrometer; and (b) each reflected pulse, respectively, in the set of reflected pulses, triggers an electric field pulse or change in polarization in the detector that is measured by the detector separately from any electric field pulse or change in polarization which is triggered in the detector by any other reflected pulse. In some cases: (a) the light sensor is part of an optical coherence tomography imaging system; and (b) the imaging system illuminates the sample with pulsed light. In some cases, the method further comprises: (a) calculating, based on measurements taken by the light sensor, a set of intensities of reflected light, each intensity corresponding to a single reflector in the set of reflectors; and (b) calculating an image of the sample by combining data regarding these intensities. In some cases: (a) the image comprises a set of regions; and (b) each respective region in the image of the sample corresponds to only one of the reflectors and visually represents only one of the intensities of light. In some cases, the method further comprises generating an optical coherence tomography image based on measurements, taken by the light sensor, of reflected light from the reflectors. In some cases: (a) the method further comprises calculating an image, based on measurements taken by the light sensor; (b) the light sensor and the reflectors are part of an imaging system; (c) the image includes a first region and a second region; (d) the first region of the image visually represents a first intensity of light incident in a first region of the image plane of the imaging system; (e) the second region of the image visually represents a second intensity of light incident in a second region of the image plane, the first intensity being measured by the light sensor separately from the second intensity; and (f) the centers of the first and second regions, respectively, of the image plane are located at a distance from each other, in the image plane, which distance is less than the Abbe X-Y Resolution of the imaging system.

Each of the cases described above in this paragraph is an example of the method described in the first sentence of this paragraph, and is also an example of an embodiment of this invention that may be combined with other embodiments of this invention.

In some implementations, this invention is an imaging system comprising: (a) a light source; (b) a stage; (c) a set of reflectors; and (d) a light sensor; wherein (i) the stage is configured to support a sample in such a way that the sample is above the set of reflectors, (ii) the set of reflectors are staggered in depth, each reflector, respectively, in the set being at a different depth than that of each other reflector in the set, and (iii) the imaging system is configured in such a way that, during a period when the stage supports the sample (A) light emitted by the light source passes through the sample, reflects from the set of reflectors, passes through the sample again and travels to the light sensor, and (B) for each respective reflector in the set, the light reflecting from the respective reflector (1) arrives at the light sensor during a time interval that is different than each time interval during which light reflecting another reflector in the set arrives at the light sensor, and (2) is measured by the light sensor separately from light reflecting from each other reflector, respectively, in the set. In some cases, the light source is configured to emit pulses of light. In some cases: (a) the light source is configured to emit pulses of light that pass through the sample and reach the reflectors; and (b) the imaging system is configured in such a way that, for each of the pulses, respectively (i) a set of multiple reflected pulses reflects from the set of reflectors, and (ii) each reflected pulse in the set of reflected pulses arrives at the light sensor during a time interval that is different than that during which any other reflected pulse in the set of reflected pulses arrives at the light sensor. In some cases, the light sensor is configured to separately measure each reflected pulse, respectively, in the set of reflected pulses. In some cases: (a) the light sensor comprises a terahertz time-domain spectroscopy detector; and (b) the detector is configured in such a way that each reflected pulse, respectively, in the set of reflected pulses, triggers an electric field pulse or change in polarization in the detector that is measured by the detector separately from any electric field pulse or change in polarization which is triggered in the detector by any other reflected pulse. In some cases, the imaging system is configured to generate an optical coherence tomography image based on measurements, taken by the light sensor, of reflected light from the reflectors. In some cases, the imaging system further comprises one or more computers that are programmed: (a) to calculate, based on measurements taken by the light sensor, a set of intensities of reflected light, each intensity corresponding to a single reflector in the set of reflectors; and (b) to calculate an image of the sample by combining data regarding these intensities. In some cases: (a) the image comprises a set of regions; and (b) each respective region in the image of the sample corresponds to only one of the reflectors and visually represents only one intensity in the set of intensities of reflected light. In some cases: (a) the imaging system further comprises one or more computers that are programmed to calculate an image, in such a way that (i) the image includes a first region and a second region, (ii) the first region of the image visually represents a first intensity of light incident in a first region of the image plane of the imaging system, and (iii) the second region of the image visually represents a second intensity of light incident in a second region of the image plane; (b) the light sensor is configured to measure the first intensity separately from the second intensity; and (c) the imaging system is configured in such a way that the centers of the first and second regions, respectively, of the image plane are located at a distance from each other, in the image plane, which distance is less than the Abbe X-Y Resolution of the imaging system. Each of the cases described above in this paragraph is an example of the imaging system described in the first sentence of this paragraph, and is also an example of an embodiment of this invention that may be combined with other embodiments of this invention.

In some implementations, this invention is a method comprising illuminating a sample in such a way that light passes through the sample, reflects from a set of reflectors, passes through the sample again and travels to a light sensor, wherein: (a) the reflectors in the set are located beneath the sample and are staggered in depth, each reflector being at a different depth than the other reflectors in the set; and (b) light reflecting from each reflector, respectively, in the set (i) has a phase, when arriving at the light sensor, that is different than the phase that light reflecting from each other reflector in the set, respectively, has when arriving at the light sensor, and (ii) is measured by the light sensor separately from light reflecting from each other reflector, respectively, in the set. In some cases, the light that passes through the sample is not pulsed. In some cases: (a) the light sensor is part of an optical coherence tomography imaging system; and (b) the imaging system illuminates the sample with light that is not pulsed. In some cases, the method further comprises: (a) calculating, based on measurements taken by the light sensor, a set of intensities of reflected light, each intensity corresponding to a single reflector in the set of reflectors; and (b) calculating an image of the sample by combining data regarding these intensities. In some cases: (a) the image comprises a set of regions; and (b) each respective region in the image of the sample corresponds to only one of the reflectors and visually represents only one of the intensities of light. In some cases: (a) the light sensor and the reflectors are part of an imaging system; (b) the image includes a first region and a second region; (c) the first region of the image visually represents a first intensity of light incident in a first region of the image plane of the imaging system; (d) the second region of the image visually represents a second intensity of light incident in a second region of the image plane, the first intensity being measured by the light sensor separately from the second intensity; and (e) the centers of the first and second regions, respectively, of the image plane are located at a distance from each other, in the image plane, which distance is less than the Abbe X-Y Resolution of the imaging system. In some cases: (a) the method further comprises calculating an image, based on measurements taken by the light sensor; (b) the light sensor and the reflectors are part of an imaging system; (c) the image includes a first region and a second region; (d) the first region of the image visually represents a first intensity of light incident in a first region of the image plane of the imaging system; (e) the second region of the image visually represents a second intensity of light incident in a second region of the image plane, the first intensity being measured by the light sensor separately from the second intensity; and (f) the centers of the first and second regions, respectively, of the image plane are located at a distance from each other, in the image plane, which distance is less than the Abbe X-Y Resolution of the imaging system. Each of the cases described above in this paragraph is an example of the method described in the first sentence of this paragraph, and is also an example of an embodiment of this invention that may be combined with other embodiments of this invention.

In some implementations, this invention is an imaging system comprising: (a) an active light source; (b) a stage; (c) a set of reflectors; and (d) a light sensor; wherein (i) the stage is configured to support a sample in such a way that the sample is above the set of reflectors, (ii) the set of reflectors are staggered in depth, each reflector, respectively, in the set being at a different depth than that of each other reflector in the set, (iii) the imaging system is configured in such a way that, during a period when the stage supports the sample (A) light emitted by the active light source passes through the sample, reflects from the set of reflectors, passes through the sample again and travels to the light sensor, and (B) for each respective reflector in the set, the light reflecting from the respective reflector (1) has a phase, when arriving at the light sensor, that is different than the phase that light reflecting from each other reflector in the set, respectively, has when arriving at the light sensor, and (2) is measured by the light sensor separately from light reflecting from each other reflector, respectively, in the set. In some cases, the imaging system is configured to generate an optical coherence tomography image based on measurements, taken by the light sensor, of reflected light from the reflectors. In some cases, the imaging system further comprises one or more computers that are programmed: (a) to calculate, based on measurements taken by the light sensor, a set of intensities of reflected light, each intensity corresponding to a single reflector in the set of reflectors, and (b) to calculate an image of the sample by combining data regarding these intensities. In some cases: (a) the image comprises a set of regions; and (b) each respective region in the image of the sample corresponds to only one of the reflectors and visually represents only one intensity in the set of intensities of reflected light. In some cases: (a) the imaging system further comprises one or more computers that are programmed to calculate an image, in such a way that (i) the image includes a first region and a second region, (ii) the first region of the image visually represents a first intensity of light incident in a first region of the image plane of the imaging system, and (iii) the second region of the image visually represents a second intensity of light incident in a second region of the image plane; (b) the light sensor is configured to measure the first intensity separately from the second intensity; and (c) the imaging system is configured in such a way that the centers of the first and second regions, respectively, of the image plane are located at a distance from each other, in the image plane, which distance is less than the Abbe X-Y Resolution of the imaging system. Each of the cases described above in this paragraph is an example of the imaging system described in the first sentence of this paragraph, and is also an example of an embodiment of this invention that may be combined with other embodiments of this invention.

Each description herein of any method or apparatus of this invention describes a non-limiting example of this invention. This invention is not limited to those examples, and may be implemented in other ways.

Each description herein of any prototype of this invention describes a non-limiting example of this invention. This invention is not limited to those examples, and may be implemented in other ways.

Each description herein of any implementation, embodiment or case of this invention (or any use scenario for this invention) describes a non-limiting example of this invention. This invention is not limited to those examples, and may be implemented in other ways.

Each Figure that illustrates any feature of this invention shows a non-limiting example of this invention. This invention is not limited to those examples, and may be implemented in other ways.

The Provisional Application does not limit the scope of this invention. The Provisional Application describes non-limiting examples of this invention, which examples are in addition to—and not in limitation of—the implementations of this invention that are described in the main part of this document. For example, if any feature described in the Provisional Application is different from, or in addition to, the features described in the main part of this document, this additional or different feature of the Provisional Application does not limit any implementation of this invention described in the main part of this document, but instead merely describes another example of this invention. As used herein, the "main part of this document" means this entire document (including any drawings listed in the Brief Description of Drawings above and any software file listed in the Computer Program Listing section above), except that the "main part of this document" does not include any document that is incorporated by reference herein.

The above description (including without limitation any attached drawings and figures) describes illustrative implementations of the invention. However, the invention may be implemented in other ways. The methods and apparatus which are described herein are merely illustrative applications of the principles of the invention. Other arrangements, methods, modifications, and substitutions by one of ordinary skill in the art are therefore also within the scope of the present invention. Numerous modifications may be made by those skilled in the art without departing from the scope of the invention. Also, this invention includes without limitation each combination and permutation of one or more of the implementations (including hardware, hardware components, methods, processes, steps, software, algorithms, features, or technology) that are described or incorporated by reference herein.

What is claimed is:

1. A method comprising illuminating a sample in such a way that light passes through the sample, reflects from a set of reflectors, passes through the sample again and travels to a light sensor, wherein:
   (a) the reflectors in the set are located beneath the sample and are staggered in depth, each reflector being at a different depth than the other reflectors in the set;
   (b) light reflecting from each reflector, respectively, in the set
      (i) arrives at the light sensor during a time interval that is different than each time interval during which light reflecting another reflector in the set arrives at the light sensor, and
      (ii) is measured by the light sensor separately from light reflecting from each other reflector, respectively, in the set;
   (c) the method further comprises calculating an image, based on measurements taken by the light sensor;
   (d) the light sensor and the reflectors are part of an imaging system;
   (e) the image includes a first region and a second region;
   (f) the first region of the image visually represents a first intensity of light incident in a first region of the image plane of the imaging system;
   (g) the second region of the image visually represents a second intensity of light incident in a second region of the image plane, the first intensity being measured by the light sensor separately from the second intensity; and (h) the centers of the first and second regions, respectively, of the image plane are located at a distance from each other, in the image plane, which distance is less than the Abbe X-Y Resolution of the imaging system.

2. An imaging system comprising:
(a) a light source;
(b) a stage;
(c) a set of reflectors; and
(d) a light sensor;
wherein
(i) the stage is configured to support a sample in such a way that the sample is above the set of reflectors,
(ii) the set of reflectors are staggered in depth, each reflector, respectively, in the set being at a different depth than that of each other reflector in the set,
(iii) the imaging system is configured in such a way that, during a period when the stage supports the sample
   (A) light emitted by the light source passes through the sample, reflects from the set of reflectors, passes through the sample again and travels to the light sensor, and
   (B) for each respective reflector in the set, the light reflecting from the respective reflector
      (1) arrives at the light sensor during a time interval that is different than each time interval during which light reflecting another reflector in the set arrives at the light sensor, and
      (2) is measured by the light sensor separately from light reflecting from each other reflector, respectively, in the set,
(iv) the imaging system further comprises one or more computers that are programmed to calculate an image, in such a way that
   (A) the image includes a first region and a second region,
   (B) the first region of the image visually represents a first intensity of light incident in a first region of the image plane of the imaging system, and
   (C) the second region of the image visually represents a second intensity of light incident in a second region of the image plane,
(v) the light sensor is configured to measure the first intensity separately from the second intensity, and
(vi) the imaging system is configured in such a way that the centers of the first and second regions, respectively, of the image plane are located at a distance from each other, in the image plane, which distance is less than the Abbe X-Y Resolution of the imaging system.

* * * * *